United States Patent
Imura et al.

(10) Patent No.: US 6,313,276 B1
(45) Date of Patent: Nov. 6, 2001

(54) HUMAN ENDOTHELIN RECEPTOR

(75) Inventors: Hiroo Imura; Kazuwa Nakao; Shigetada Nakanishi, all of Kyoto (JP)

(73) Assignee: Shionogi Sieyaku Kabushiki Kaisha, Osaka (JP)

( * ) Notice: Subject to any disclaimer, the term of this patent is extended or adjusted under 35 U.S.C. 154(b) by 0 days.

(21) Appl. No.: 08/121,446

(22) Filed: Sep. 14, 1993

Related U.S. Application Data

(63) Continuation of application No. 07/911,684, filed on Jul. 10, 1992, now abandoned.

(30) Foreign Application Priority Data

Jul. 12, 1991 (JP) .................................................. 3-172828

(51) Int. Cl.[7] .......................... C07H 21/04; C12N 15/11; C12N 15/12; C12N 15/63
(52) U.S. Cl. .................... 536/23.1; 435/69.1; 435/320.1; 435/246.1
(58) Field of Search .......................... 536/23.1; 435/69.1, 435/320.1, 240.1

(56) References Cited

FOREIGN PATENT DOCUMENTS 0480381 4/1992 (EP) .

OTHER PUBLICATIONS

Sakamoto et al., "Cloning and functional expression of human cDNA for ETB endothelin receptor" *Chem. Abstracts* (Jul. 6, 1992) 117(1):216.
Ogawa et al., "Molecular cloning of a non–isopeptide–selective human endothelin receptor" *Chem. Abstracts* (Mar. 30, 1992) 116(13):230.
Nakamuta et al., "Cloning and sequence analysis of a cDNA encoding human non–selective type of endothelin receptor" *Chem. Abstracts* (Mar. 30, 1992) 116(13):223.
Lin et al., "Cloning and functional expression of a vascular smooth muscle endothelin 1 receptor" *Chem. Abstracts* (Mar. 2, 1992) 116(9):165.
Wada et al., Biochemical Biophysical Research Communications, vol. 167, pp. 251–257, 1990.*
Shimada et al., Eur. J. Pharmacology, v. 193, pp. 123, 1991.*
Hosoda et al., FEBS Letters, 287, 23, 1991.*
Adachi et al., Biochemical and Biophysical Res. Communications, 180, 1265, 1991.*
Yanagisawa et al., *Trends in Pharmacol. Sci.* (1989) 10:374–378.
MacCumber et al., *Proc. Natl. Acad. Sci.* (1990) 87:2359–2363.
Yanagisawa et al., *Nature* (1988) 332:411–415.
Watanabe et al., *Biochem. Biophys. Res. Commun.* (1989) 161(3):1252–1259.
Martin et al., *J. Biol. Chem.* (1990) 265(23):14044–14049.
Sakurai et al., *Nature* (1990) 348:732–735.
Adachi et al., "Cloning and characterization of cDNA encoding human A–type endothelial receptor" *Biochem. Biophys. Res. Comm.* (1991) 180(3):1265–1272.
Cyr et al., "Cloning and chromosomal localization of a human endothelial ETA receptor" *Biochem. Biophys. Res. Comm.* (1991) 181(1):184–190.
Hosoda et al., "Cloning and expression of human endothelial–1 receptor cDNA" *FEBS Letters* (1991) 287(1,2):23–26.
Nakamuta et al., "Cloning and sequence analysis of a cDNA clone encoding human non–selective type of endothelin receptor" *Biochem. Biophys. Res. Comm.* (1991) 177(1):34–39.
Ogawa et al., "Molecular cloning of a non–isopeptide–selective human endothelin receptor" *Biochem. Biophys. Res. Comm.* (1991) 178(1):248–255.
Sakamoto et al., "Cloning and functional expression of human cDNA for the $ET_B$ endothelin receptor" *Biochem. Biophys. Res. Comm.* (1991) 178(2):656–663.
Arai et al., 1990, Nature, 348, 730.*
Lin et al., 1991, PNAS, 88, 3185.*
Masuda et al., 1989, FEB, 257, 208.*
Kloog et al., 1989, FEB, 253, 199.*
Inoue et al., 1989, PNAS, 86, 2863.*
Masu et al., 1987, Nature, 329, 836.*

* cited by examiner

Primary Examiner—Gary L. Kunz
(74) *Attorney, Agent, or Firm*—Morrison & Foerster LLP

(57) ABSTRACT

DNA encoding an endothelin receptor shown in SEQ ID NO: 1, SEQ ID NO: 2, SEQ ID NO: 3, or SEQ ID NO: 4. In the Sequence Listing is isolated from cDNA which is prepared from poly(A)+RNA derived from a human placenta. In addition, an expression vector containing the DNA and a transformant containing the expression vector are obtained. An endothelin receptor is obtained by culturing this transformant. A receptor shown in SEQ ID NO: 1 and SEQ ID NO: 2 is an $ET_A$-receptor which has a high affinity for endothelins 1 and 2, especially for the endothelin 1. A receptor shown in SEQ ID NO: 3 and SEQ ID NO: 4 is an $ET_B$-receptor which has an affinity for endothelins 1, 2 and 3 with no selectivity.

8 Claims, 16 Drawing Sheets

Fig. 1a

```
GAATTCGCGG CCGCCTCTTG CGGTCCCAGA GTGGAGTGGA AGGTCTGGAG CTTTGGGAGG    60
AGACGGGGAG GACAGACTGG AGGCGTGTTC CTCCCGGATT TTCTTTTTCG TGCGAGCCCT   120
CGCGCGCGCG TACAGTCATC CCGCTGGTCT GACGATTGTG GAGAGGCGGT GGAGAGGCTT   180
CATCCATCCC ACCCGGTCGT CGCCGGGGAT TGGGGTCCCA GCGACACCTC CCCGGGAGAA   240
GCAGTGCCCA GGAAGTTTTC TGAAGCCGGG GAAGCTGTGC AGCCGAAGCC GCCGCCGCGC   300
CGGAGCCCGG GACACCGGCC ACCCTCCGCG CCACCCACCC TCGCTTTCTC CGGCTTCCTC   360
TGGCCCAGGC GCCGCGCGGA CCCGGCAGCT GTCTGCGCAC GCCGAGCTCC ACGGTGAAAA   420
AAAAAGTGAA GGTGTAAAAG CAGCACAAGT GCAATAAGAG ATATTTCCTC AAATTTGCCT   480
CAAG ATG GAA ACC CTT TGC CTC AGG GCA TCC TTT TGG CTG GCA CTG GTT   529
     Met Glu Thr Leu Cys Leu Arg Ala Ser Phe Trp Leu Ala Leu Val
     -20             -15             -10
                                                                    577
GGA TGT GTA ATC AGT GAT AAT CCT GAG AGA TAC AGC ACA AAT CTA AGC
Gly Cys Val Ile Ser Asp Asn Pro Glu Arg Tyr Ser Thr Asn Leu Ser
-5              -1  1               5                   10
AAT CAT GTG GAT GAT TTC ACC ACT TTT CGT GGC ACA GAG CTC AGC TTC    625
Asn His Val Asp Asp Phe Thr Thr Phe Arg Gly Thr Glu Leu Ser Phe
            15                  20                  25
CTG GTT ACC ACT CAT CAA CCC ACT AAT TTG GTC CTA CCC AGC AAT GGC    673
Leu Val Thr Thr His Gln Pro Thr Asn Leu Val Leu Pro Ser Asn Gly
            30                  35                  40
TCA ATG CAC AAC TAT TGC CCA CAG CAG ACT AAA ATT ACT TCA GCT TTC    721
Ser Met His Asn Tyr Cys Pro Gln Gln Thr Lys Ile Thr Ser Ala Phe
            45                  50                  55
AAA TAC ATT AAC ACT GTG ATA TCT TGT ACT ATT TTC ATC GTG GGA ATG    769
Lys Tyr Ile Asn Thr Val Ile Ser Cys Thr Ile Phe Ile Val Gly Met
60                  65                  70                  75
```

Fig. 1b

```
GTG GGG AAT GCA ACT CTG CTC AGG ATC ATT TAC CAG AAC AAA TGT ATG        817
Val Gly Asn Ala Thr Leu Leu Arg Ile Ile Tyr Gln Asn Lys Cys Met
             80                  85                  90
AGG AAT GGC CCC AAC GCG CTG ATA GCC AGT CTT GCC CTT GGA GAC CTT        865
Arg Asn Gly Pro Asn Ala Leu Ile Ala Ser Leu Ala Leu Gly Asp Leu
             95                  100                 105
ATC TAT GTG GTC ATT GAT CTC CCT ATC AAT GTA TTT AAG CTG CTG GCT        913
Ile Tyr Val Val Ile Asp Leu Pro Ile Asn Val Phe Lys Leu Leu Ala
             110                 115                 120
GGG CGC TGG CCT TTT GAT CAC AAT GAC TTT GGC GTA TTT CTT TGC AAG        961
Gly Arg Trp Pro Phe Asp His Asn Asp Phe Gly Val Phe Leu Cys Lys
             125                 130                 135
CTG TTC CCC TTT TTG CAG AAG TCC TCG GTG GGG ATC ACC GTC CTC AAC       1009
Leu Phe Pro Phe Leu Gln Lys Ser Ser Val Gly Ile Thr Val Leu Asn
140                 145                 150                 155
CTC TGC GCT CTT AGT GTT GAC AGG TAC AGA GCA GTT GCC TCC TGG AGT       1057
Leu Cys Ala Leu Ser Val Asp Arg Tyr Arg Ala Val Ala Ser Trp Ser
             160                 165                 170
CGT GTT CAG GGA ATT GGG ATT CCT TTG GTA ACT GCC ATT GAA ATT GTC       1105
Arg Val Gln Gly Ile Gly Ile Pro Leu Val Thr Ala Ile Glu Ile Val
             175                 180                 185
TCC ATC TGG ATC CTG TCC TTT ATC CTG GCC ATT CCT GAA GCG ATT GGC       1153
Ser Ile Trp Ile Leu Ser Phe Ile Leu Ala Ile Pro Glu Ala Ile Gly
             190                 195                 200
TTC GTC ATG GTA CCC TTT GAA TAT AGG GGT GAA CAG CAT AAA ACC TGT       1201
Phe Val Met Val Pro Phe Glu Tyr Arg Gly Glu Gln His Lys Thr Cys
             205                 210                 215
```

Fig. 1c

| | |
|---|---|
| ATG CTC AAT GCC ACA TCA AAA TTC ATG GAG TTC TAC CAA GAT GTA AAG<br>Met Leu Asn Ala Thr Ser Lys Phe Met Glu Phe Tyr Gln Asp Val Lys<br>220                    225                    230                    235 | 1249 |
| GAC TGG TGG CTC TTC GGG TTC TAT TTC TGT ATG CCC TTG GTG TGC ACT<br>Asp Trp Trp Leu Phe Gly Phe Tyr Phe Cys Met Pro Leu Val Cys Thr<br>                  240                    245                    250 | 1297 |
| GCG ATC TTC TAC ACC CTC ATG ACT TGT GAG ATG TTG AAC AGA AGG AAT<br>Ala Ile Phe Tyr Thr Leu Met Thr Cys Glu Met Leu Asn Arg Arg Asn<br>                  225                    260                    265 | 1345 |
| GGC AGC TTG AGA ATT GCC CTC AGT GAA CAT CTT AAG CAG CGT CGA GAA<br>Gly Ser Leu Arg Ile Ala Leu Ser Glu His Leu Lys Gln Arg Arg Glu<br>                  270                    275                    280 | 1393 |
| GTG GCA AAA ACA GTT TTC TGC TTG GTT GTA ATT TTT GCT CTT TGC TGG<br>Val Ala Lys Thr Val Phe Cys Leu Val Val Ile Phe Ala Leu Cys Trp<br>                  285                    290                    295 | 1441 |
| TTC CCT CTT CAC TTA AGC CGT ATA TTG AAG AAA ACT GTG TAT AAC GAA<br>Phe Pro Leu His Leu Ser Arg Ile Leu Lys Lys Thr Val Tyr Asp Glu<br>300                    305                    310                    315 | 1489 |
| ATG GAC AAG AAC CGA TGT GAA TTA CTT AGT TTC TTA CTG CTC ATG GAT<br>Met Asp Lys Asn Arg Cys Glu Leu Leu Ser Phe Leu Leu Leu Met Asp<br>                  320                    325                    330 | 1537 |
| TAC ATC GGT ATT AAC TTG GCA ACC ATG AAT TCA TGT ATA AAC CCC ATA<br>Tyr Ile Gyr Ile Asn Leu Ala Thr Met Asn Ser Cys Lle Asn Pro Ile<br>                  335                    340                    345 | 1585 |
| GCT CTG TAT TTT GTG AGC AAG AAA TTT AAA AAT TGT TTC CAG TCA TGC<br>Ala Leu Tyr Phe Val Ser Lys Lys Phe Lys Asn Cys Phe Gln Ser Cys<br>                  350                    355                    360 | 1633 |

Fig. 1d

| | |
|---|---|
| CTC TGC TGC TGC TGT TAC CAG TCC AAA AGT CTG ATG ACC TCG GTC CCC<br>Leu Cys Cys Cys Cys Tyr Gln Ser Lys Ser Leu Met Thr Ser Val Pro<br>365               370              375 | 1681 |
| ATG AAC GGA ACA AGC ATC CAG TGG AAG AAC CAC GAT CAA AAC AAC CAC<br>Met Asn Gly Thr Ser Ile Gln Trp Lys Asn His Asp Gln Asn Asn His<br>380             385            390           395 | 1729 |
| AAC ACA GAC CGG AGC AGC CAT AAG GAC AGC ATG AAC TGACCACCCT<br>Asn Thr Asp Arg Ser Ser His Lys Asp Ser Met Asn<br>400             405 | 1775 |
| TAGAAGCACT CCTCGGTACT CCCATAATCC TCTCGGAGAA AAAAATCACA AGGCAACTGT | 1835 |
| GACTCCGGGA ATCTCTTCTC TGATCCTTCT TCCTTAATTC ACTCCCACAC CCAAGAAGAA | 1895 |
| ATGCTTTCCA AAACCGCAAG GTAGACTGGT TTATCCACCC ACAACATCTA CGAATCGTAC | 1955 |
| TTCTTTAATT GATCTA<u>ATTT A</u>CATATTCTG CGTGTTGTAT TCAGCACTAA AAAATGGTGG | 2015 |
| GAGCTGGGGG AGAATGAAGA CTGTTAAATG AAACCAGAAG GAT<u>ATTTACT</u> ACTTTTGCAT | 2075 |
| GAAAATAGAG CTTTCAAGTA CATGGCTAGC TTTTATGGCA GTTCTGGTGA ATGTTCAATG | 2135 |
| GGAACTGGTC ACCATGAAAC TTTAGAGATT AACGACAAGA TTTTCTACTT TTTTTAAGTG | 2195 |
| ATTTTTTGTC CTTCAGCCAA ACACAATATG GGCTCAGGTC ACTTTTATTT GAAATGTCAT | 2255 |
| TTGGTGCCAG TATTTTTTAA CTGCATAATA GCCTAACATG ATTATTTGAA CTT<u>ATTTA</u>CA | 2315 |
| CATAGTTTGA AAAAAAAAAG ACAAAAATAG TATTCAGGTG AGCAATTAGA TTAGTATTTT | 2375 |
| CCACGTCACT <u>ATTT</u>ATTTTT TTAAAACACA AATTCTAAAG CTACAACAAA TACTACAGGC | 2435 |
| CCTTAAAGCA CAGTCTGATG ACACATTTGG CAGTTTAATA GATGTTACTC AAAGAATTTT | 2495 |
| TTAAGAACTG TATTTTATTT TTTAAATGGT GTTTTATTAC AAGGGACCTT GAACATGTTT | 2555 |
| TGTATGTTAA ATTCAAAAGT AATGCTTCAA TCAGATAGTT CTTTTTCACA AGTTCAATAC | 2615 |
| TGTTTTTCAT GTAAATTTTG TATGAAAAAT CAATGTCAAG TACCAAAATG TTAATGTATG | 2675 |
| TGTC<u>ATTTAA</u> CTCTGCCTGA GACTTTCAGT GCACTGTATA TAGAAGTCTA AAACACACCT | 2735 |
| AAGAGAAAAA GATCGAATTT TTCAGATGAT TCGGAAATTT TCATTCAGGT ATTTGTAATA | 2795 |

Fig. 1e

```
GTGACATATA TATGTATATA CATATCACCT CCTATTCTCT TAATTTTTGT TAAAATGTTA    2855
ACTGGCAGTA AGTCTTTTTT GATCATTCCC TTTTCCATAT AGGAAACATA ATTTTGAAGT    2915
GGCCAGATGA GTTTATCATG TCAGTGAAAA ATAATTACCC ACAAATGCCA CCAGTAACTT    2975
AACGATTCTT CACTTCTTGG GGTTTTCAGT ATGAACCTAA CTCCCCACCC CAACATCTCC    3035
CTCCCACATT GTCACCATTT CAAAGGGCCC ACAGTGACTT TGCTGGGCA TTTTCCCAGA    3095
TGTTTACAGA CTGTGAGTAC AGCAGAAAAT CTTTTACTAC TGTGTGTGTG TATATATATA    3155
AACAATTGTA AATTTCTTTT AGCCCATTTT TCTAGACTGT CTCTGTGGAA TATATTTGTG    3215
TGTGTGATAT ATGCATGTGT GTGATGGTAT GTATGGATTT AATCTAATCT AATAATTGTG    3275
CCCCGCAGTT GTGCCAAAGT GCATAGTCTG AGCTAAAATC TAGGTGATTG TTCATCATGA    3335
CACCCTGCCT CAGTCCATTT TAACCTGTAG CAACCTTCTG CATTCATAAA TCTTGTAATC    3395
ATGTTACCAT TACAAATGGG ATATAAGAGG CAGCGTGAAA GCAGATGAGC TGTGGACTAG    3455
CAATATAGGG TTTTGTTTGG TTGGTTGGTT TGATAAAGCA GTATTTGGGG TCATATTGTT    3515
TCCTGTGCTG GAGCAAAAGT CATTACACTT TGAAGTATTA TATTGTTCTT ATCCTCAATT    3575
CAATGTGGTG ATGAAATTGC CAGGTTGTCT GATATTTCTT TCAGACTTCG CCAGACAGAT    3635
TGCTGATAAT AAATTAGGTA AGATAATTTG TTGGGCCATA TTTTAGGACA GGTAAAATAA    3695
CATCAGGTTC CAGTTGCTTG AATTGCAAGG CTAAGAAGTA CTGCCCTTTT GTGTGTTAGC    3755
AGTCAAATCT ATTATTCCAC TGGCGCATCA TATGCAGTGA TATATGCCTA TAATATAAGC    3815
CATAGGTTCA CACCATTTTG TTTAGACAAT TGTCTTTTTT TCAAGATGCT TTGTTTCTTT    3875
CATATGAAAA AAATGCATTT TATAAATTCA GAAAGTCATA GATTTCTGAA GGCGTCAACG    3935
TGCATTTTAT TTATGGACTG GTAAGTAACT GTGGTTTACT AGCAGGAATA TTTCCAATTT    3995
CTACCTTTAC TACATCTTTT CAACAAGTAA CTTTGTAGAA ATGAGCCAGA AGCCAAGGCC    4055
CTGAGTTGGC AGTGGCCCAT AAGTGTAAAA TAAAAGTTTA CAGAAACCTT               4105
```

Fig. 2a

| | |
|---|---|
| GAGACATTCC GGTGGGGGAC TCTGGCCAGC CCGAGCAACG TGGATCCTGA GAGCACTCCC | 60 |
| AGGTAGGCAT TTGCCCCGGT GGGACGCCTT GCCAGACCAG TGTGTGGCAG GCCCCCGTGG | 120 |
| AGGATCAACA CAGTGGCTGA ACACTGGGAA GGAACTGGTA CTTGGAGTCT GGACATCTGA | 180 |
| AACTTGGCTC TGAAACTGCG GAGCGGCCAC CGGACGCCTT CTGGAGCAGG TAGCAGC | 237 |

```
ATG CAG CCG CCT CCA AGT CTG TGC GGA CGC GCC CTG GTT GCG CTG GTT      285
Met Gln Pro Pro Pro Ser Leu Cys Gly Arg Ala Leu Val Ala Leu Val
 1               5                  10                 15

CTT GCC TGC GGC CTG TCG CGG ATC TGG GGA GAG GAG AGA GGC TTC CCG      333
Leu Ala Cys Gly Leu Ser Arg Ile Trp Gly Glu Glu Arg Gly Phe Pro
            20                  25                 30

CCT GAC AGG GCC ACT CCG CTT TTG CAA ACC GCA GAG ATA ATG ACG CCA      381
Pro Asp Arg Ala Thr Pro Leu Leu Gln Thr Ala Glu Ile Met Thr Pro
       35                  40                 45

CCC ACT AAG ACC TTA TGG CCC AAG GGT TCC AAC GCC AGT CTG GCG CGG      429
Pro Thr Lys Thr Leu Trp Pro Lys Gly Ser Asn Ala Ser Leu Ala Arg
  50                  55                 60

TCG TTG GCA CCT GCG GAG GTG CCT AAA GGA GAC AGG ACG GCA GGA TCT      477
Ser Leu Ala Pro Ala Glu Val Pro Lys Gly Asp Arg Thr Ala Gly Ser
 65             70                  75                 80

CCG CCA CGC ACC ATC TCC CCT CCC CCG TGC CAA GGA CCC ATC GAG ATC      525
Pro Pro Arg Thr Ile Ser Pro Pro Pro Cys Gln Gly Pro Ile Glu Ile
            85                  90                 95

AAG GAG ACT TTC AAA TAC ATC AAC ACG CTT GTC TGC CTT GTG TTC          573
Lys Glu Thr Phe Lys Tyr Ile Asn Thr Val Val Ser Cys Leu Val Phe
              100                 105                110
```

Fig. 2b

```
    GTG CTG GGG ATC ATC GGG AAC TCC ACA CTT CTG AGA ATT ATC TAC AAG            621
    Val Leu Gly Ile Ile Gly Asn Ser Thr Leu Leu Arg Ile Ile Tyr Lrs
                115             120             125
    AAC AAG TGC ATG CGA AAC GGT CCC AAT ATC TTG ATC GCC AGC TTG GCT            669
    Asn Lys Gys Met Arg Asn Gly Pro Asn Ile Leu Ile Ala Ser Leu Ala
                130             135             140
    CTG GGA GAC CTG CTG CAC ATC GTC ATT GAC ATC CCT ATC AAT GTC TAC            717
    Leu Gly Asp Leu Leu His Ile Val Ile Asp Ile Pro Ile Asn Val Tyr
    145             150             155             160
    AAG CTG CTG GCA GAG GAC TGG CCA TTT GGA GCT GAG ATG TGT AAG CTG            765
    Lys Leu Leu Ala Glu Asp Trp Pro Phe Gly Ala Glu Met Cys Lys Leu
                165             170             175
    GTG CCT TTC ATA CAG AAA GCC TCC GTG GGA ATC ACT GTG CTG AGT CTA            813
    Val Pro Phe Ile Gln Lys Ala Ser Val Gly Ile Thr Val Leu Ser Leu
                180             185             190
    TGT GCT CTG AGT ATT GAC AGA TAT CGA GCT GTT GCT TCT TGG AGT AGA            861
    Cys Ala Leu Ser Ile Asp Arg Tyr Arg Ala Val Ala Ser Trp Ser Arg
                195             200             205
    ATT AAA GGA ATT GGG GTT CCA AAA TGG ACA GCA GTA GAA ATT GTT TTG            909
    Ile Lys Gly Ile Gly Val Pro Lys Trp Thr Ala Val Glu Ile Val Leu
                210             215             220
    ATT TGG GTG GTC TCT GTG GTT CTG GCT GTC CCT GAA GCC ATA GGT TTT            957
    Ile Trp Val Val Ser Val Val Leu Ala Val Pro Glu Ala Ile Gly Phe
    225             230             235             240
    GAT ATA ATT ACG ATG GAC TAC AAA GGA AGT TAT CTG CGA ATC TGC TTG            1005
    Asp Ile Ile Thr Met Asp Tyr Lys Gly Ser Tyr Leu Arg Ile Cys Leu
                245             250             255
```

Fig. 2c

| | |
|---|---|
| CTT CAT CCC GTT CAG AAG ACA GCT TTC ATG CAG TTT TAC AAG ACA GCA | 1053 |
| Leu His Pro Val Gln Lys Thr Ala Phe Met Gln Phe Tyr Lys Thr Ala | |
|            260                 265                270 | |
| AAA GAT TGG TGG CTG TTC AGT TTC TAT TTC TGC TTG CCA TTG GCC ATC | 1101 |
| Lys Asp Typ Trp Leu Phe Ser Phe Tyr Phe Cys Leu Pro Leu Ala Ile | |
|    275                280               285 | |
| ACT GCA TTT TTT TAT ACA CTA ATG ACC TGT GAA ATG TTG AGA AAG AAA | 1149 |
| Thr Ala Phe Phe Tyr Thr Leu Met Thr Cys Glu Met Leu Arg Lys Lys | |
|    290                295               300 | |
| AGT GGC ATG CAG ATT GCT TTA AAT GAT CAC CTA AAG CAG AGA CGG GAA | 1197 |
| Ser Gly Met Gln Ile Ala Leu Asn Asp His Leu Lys Gln Arg Arg Glu | |
| 305           310               315              320 | |
| GTG GCC AAA ACC GTC TTT TGC CTG GTC CTT GTC TTT GCC CTC TGC TGG | 1245 |
| Val Ala Lys Thr Val Phe Cys Leu Val Leu Val Phe Ala Leu Cys Trp | |
|                   325               330             335 | |
| CTT CCC CTT CAC CTC AGC AGG ATT CTG AAG CTC ACT GTT TAT AAT CAG | 1293 |
| Leu Pro Leu His Leu Ser Arg Ile Leu Lys Leu Thr Leu Tyr Asp Gln | |
|                   340               345             350 | |
| AAT GAT CCC AAT AGA TGT GAA CTT TTG AGC TTT CTG TTG GTA TTG GAC | 1341 |
| Asn Asp Pro Asn Arg Cys Glu Leu Leu Ser Phe Leu Leu Val Leu Asp | |
|         355                360               365 | |
| TAT ATT GGT ATG AAC ATG GCT TCA CTG AAT TCC TGC ATT AAC CCA ATT | 1389 |
| Tyr Ile Gyr Ile Asn Met Ala Ser Leu Asn Ser Cys Ile Asn Pro Ile | |
|                 370               375             380 | |
| GCT CTG TAT TTC GTG AGC AAA AGA TTC AAA AAC TGC TTT AAG TCA TGC | 1437 |
| Ala Leu Tyr Leu Val Ser Lys Arg Phe Lys Asn Cys Phe Lys Ser Cys | |
| 385              390               395              400 | |

Fig. 2d

```
TTA TGC TGC TGG TGC CAG TCA TTT GAA GAA AAA CAG TCC TTG GAG GAA    1485
Leu Cys Cys Trp Cys Gln Ser Phe Glu Glu Lys Gln Ser Leu Glu Glu
             405                 410                 415
AAG CAG TCG TGC TTA AAG TTC AAA GCT AAT GAT CAC GGA TAT GAC AAC    1533
Lys Gln Ser Cys Leu Lys Phe Lys Ala Asn Asp His Gly Tyr Asp Asn
             420                 425                 430
TTC CGT TCC AGT AAT AAA TAC AGC TCA TCT TGAAAGAAGA ACTATTCACT      1583
Phe Arg Ser Ser Asn Lys Tyr Ser Ser Ser
             435                 440
GTATTTCATT TTCTTTATAT TGGACGGAAG TCATTAAAAC AAAATGAAAC ATTTGCCAAA  1643
ACAAAACAAA AAACTATGTA TTTGCACAGC ACACTATTAA AATATTAAGT GTAATTATTT  1703
TAACACTCAC AGCTACATAT GACATTTTAT GAGCTGTTTA CGGCATGGAA AGAAAATCAG  1763
AGGGAATTAA GAAAGCCTCG TCGTGAAAGC ACTTAATTTT TTACAGTTAG CACTTCAACA  1823
TAGCTCTTAA CAACTTCCAG GATATTCACA CAACACTTAG GCTTAAAAAT GAGCTCACTC  1883
AGAATTTCTA TTCTTTCTAA AAAGAGATTT ATTTTTAAAT CAATGGGACT CTGATATAAA  1943
GGAAGAATAA GTCACTGTAA AACAGAACTT TTAAATGAAG CTTAAATTAC TCAATTTAAA  2003
ATTTTAAAAT CCTTTAAAAC AACTTTTCAA TTAATATTAT CACACTATTA TCAGATTGTA  2063
ATTAGATGCA AATGAGAGAG CAGTTTAGTT GTTGCATTTT TCGGACACTG GAAAGATTTA  2123
AATGATCAGG AGGGAGTAAC AGAAAGAGCA AGGCTGTTTT TGAAATTCAT TACACTTTCA  2183
CTAGAAGCCC AAACCTCAGC ATTCTGCAAT ATGTAACCAA CATGTCACAA ACAAGCAGCA  2243
TGTAACAGAC TGGCACATGT GCCAGCTGAA TTTAAAATAT AATACTTTTA AAAAGAAAAT  2303
TATTACATCC TTTACATTCA GTTAAGATCA AACCTCACAA AGAGAAATAG AATGTTTGAA  2363
AGGCTATCCC AAAAGACTTT TTTGAATCTG TCATTCACAT ACCCTGTGAA GACAATACTA  2423
TCTACAATTT TTTCAGGATT ATTAAAATCT TCTTTTTTCA CTATCGTAGC TTAAACTCTG  2483
TTTGGTTTTG TCATCTGTAA ATACTTACCT ACATACACTG CATGTAGATG ATTAAATGAG  2543
GGCAGGCCCT GTGCTCATAG CTTTACGATG GAGAGATGCC AGTGACCTCA TAATAAAGAC  2603
TGTGAACTGC CTGGTGCAGT GTCCACATGA CAAAGGGGCA GGTAGCACCC TCTCTCACCC  2663
```

Fig. 2e

```
ATGCTGTGGT TAAAATGGTT TCTAGCATAT GTATAATGCT ATAGTTAAAA TACTATTTTT    2723
CAAAATCATA CAGATTAGTA CATTTAACAG CTACCTGTAA AGCTTATTAC TAATTTTTGT    2783
ATTATTTTTG TAAATAGCCA ATAGAAAAGT TGCTTGACA TGGTGCTTTT CTTTCATCTA    2843
GAGGCAAAAC TGCTTTTTGA GACCGTAAGA ACCTCTTAGC TTTGTGCGTT CCTGCCTAAT    2903
TTTTATATCT TCTAAGCAAA GTGCCTTAGG ATAGCTTGGG ATGAGATGTG TGTGAAAGTA    2963
TGTACAAGAG AAAACGGAAG AGAGAGGAAA TGAGGTGGGG TTGGAGGAAA CCCATGGGGA    3023
CAGATTCCCA TTCTTAGCCT AACGTTCGTC ATTGCCTCGT CACATCAATG CAAAAGGTCC    3083
TGATTTTGTT CCAGCAAAAC ACAGTGCAAT GTTCTCAGAG TGACTTTCGA AATAAATTGG    3143
GCCCAAGAGC TTTAACTCGG TCTTAAAATA TGCCCAAATT TTTACTTTGT TTTTCTTTTA    3203
ATAGGCTGGG CCACATGTTG GAAATAAGCT AGTAATGTTG TTTTCTGTCA ATATTGAATG    3263
TGATGGTACA GTAAACCAAA ACCCAACAAT GTGGCCAGAA AGAAAGAGCA ATAATAATTA    3323
ATTCACACAC CATATGGATT CTATTTATAA ATCACCCACA AACTTGTTCT TTAATTTCAT    3383
CCCAATCACT TTTTCAGAGG CCTGTTATCA TAGAAGTCAT TTTAGACTCT CAATTTTAAA    3443
TTAATTTTGA ATCACTAATA TTTTCACAGT TTATTAATAT ATTTAATTTC TATTTAAATT    3503
TTAGATTATT TTTATTACCA TGTACTGAAT TTTTACATCC TGATACCCTT TCCTTCTCCA    3563
TGTCAGTATC ATGTTCTCTA ATTATCTTGC CAAATTTTGA AACTACACAC AAAAAGCATA    3623
CTTGCATTAT TTATAATAAA ATTGCATTCA GTGGCTTTTT AAAAAAAATG TTTGATTCAA    3683
AACTTTAACA TACTGATAAG TAAGAAACAA TTATAATTTC TTTACATACT CAAAACCAAG    3743
ATAGAAAAAG GTGCTATCGT TCAACTTCAA AACATGTTTC CTAGTATTAA GGACTTTAAT    3803
ATAGCAACAG ACAAAATTAT TGTTAACATG GATGTTACAG CTCAAAAGAT TTATAAAAGA    3863
TTTTAACCTA TTTTCTCCCT TATTATCCAC TGCTAATGTG GATGTATGTT CAAACACCTT    3923
TTAGTATTGA TAGCTTACAT ATGGCCAAAG GAATACAGTT TATAGCAAAA CATGGGTATG    3983
CTGTAGCTAA CTTTATAAAA GTGTAATATA ACAATGTAAA AAATTATATA TCTGGGAGGA    4043
TTTTTTGGTT GCCTAAAGTG GCTATAGTTA CTGATTTTTT ATTATGTAAG CAAAACCAAT    4103
AAAAATTTAA GTTTTTTTAA CAACTACCTT ATTTTTCACT GTACAGACAC TAATTCATTA    4163
AATACTAATT GATTGTTTAA AAGAAATATA AATGTGACAA GTGGACATTA TTTATGTTAA    4223
ATATACAATT ATCAAGCAAG TATGAAGTTA TTCAATTAAA ATGCCACATT TCTGGTCTCT    4283
GGGAAAAAAA AAAAAAAA                                                  4301
```

HUMAN ENDOTHELIN RECEPTOR

This application is a continuation, of application Ser. 07/911,684, filed Jul. 10, 1992, abandoned.

BACKGROUND OF THE INVENTION

1. Field of the Invention

The present invention relates to a human endothelin receptor, DNA sequence encoding the receptor, an expression vector carrying the DNA sequence, a transformant comprising the expression vector, and a method for producing a human endothelin receptor from the transformant.

2. Description of the Prior Art

An endothelin receptor (ET-receptor) is a receptor for an endothelin (ET). ET-receptors derived from animals such as bovines and rats have been known. An ET is a peptide present in various tissues in animals and is known as a strong vasoconstrictor. Cloning and sequence analysis of known ET genes have revealed that the ETs comprise three kinds of isopeptides: Endothelin 1 (ET-1), Endothelin 2 (ET-2), and Endothelin 3 (ET-3). Thereafter, it has been found that these ETs are distributed in a wide variety of vascular and non-vascular tissues (Proc. Natl. Acad. Sci. U.S.A. 86, 2863–2867 (1989); Trends in Pharmacol. Sci. 10, 374–378 (1989); and Proc. Natl. Acad. Sci. U.S.A. 87, 2359–2363 (1990)). ET-1 has initially been identified as a strong vasoconstrictive peptide with 21-amino-acid residues produced by porcine vascular endothelial cells (Nature, 332, 411–415 (1988)).

It has previously been shown in vivo that ET-1 and ET-2 are much more strong vasoconstrictors than ET-3, whereas the three ET isopeptides are roughly equipotent in producing the transient vasodilation.

As described above, the analysis of nucleic acid sequences of ETs has revealed that various kinds of ET isopeptides exist. These ET isopeptides are also different in their properties. Therefore, it appears that various subtypes of ET-receptors exist. The existence of various subtypes of ET-receptors has been proved by the radioactive ligand binding studies of Watanabe, H. et al. (Biochem. Biophys. Res. Commun., 161, 1252–1259 (1989)), and Martin, E. R. et al. (J. Biol. Chem. 265, 14044–14049 (1990)). These studies indicate the existence of, at least, two kinds of ET-receptors. One of them has a higher affinity for ET-1 and ET-2 than for ET-3; and the other has an affinity for ET-1, ET-2, and ET-3 with no selectivity.

The ET-receptor is useful as a reagent for measuring the amount of ET or useful in screening for an antagonist of the ET-receptor so as to study agents for the circulatory system. Therefore, there is a demand for a structure analysis of the ET-receptor and effective production of the ET-receptor by means of genetic engineering using the information of this structural analysis.

SUMMARY OF THE INVENTION

The human endothelin receptor of the present invention comprises amino acid sequence from Asp at +1 to Asn at +407 shown in SEQ ID NO:1 and SEQ. ID NO:2.

The human endothelin receptor of the present invention comprises amino acid sequence from Met at −20 to Asn at +407 shown in SEQ ID NO:1 and SEQ ID NO:2.

The DNA sequence of the present invention encodes the human endothelin receptor comprising amino acid sequence from Asp at +1 to Asn at +407 shown in SEQ ID NO:1 and SEQ ID NO:2.

The human endothelin receptor of the present invention comprises amino acid sequence from Glu at +27 to Ser at +442 shown in SEQ ID NO:3 and SEQ ID NO:4.

The human endothelin receptor of the present invention comprises amino acid sequence from Met at +1 to Ser at +442 shown in SEQ ID NO:3 and SEQ ID NO:4.

The DNA sequence of the present invention encodes the human endothelin receptor comprising amino acid sequence from Glu at +27 to Ser at +442 shown in SEQ ID NO:3 and SEQ ID NO:4.

The expression vector of the present invention comprises the DNA sequence encoding the human endothelin receptor having amino acid sequence from Asp at +1 to Asn at +407 shown in SEQ ID NO:1 and SEQ ID NO:2.

The transformant of the present invention is obtained by introducing into a host cell the expression vector comprising the DNA sequence encoding the human endothelin receptor having amino acid sequence from Asp at +1 to Asn at +407 shown in SEQ ID NO:1 and SEQ ID NO:2.

The expression vector of the present invention comprises the DNA sequence encoding the human endothelin receptor having amino acid sequence from Glu at +27 to Ser at +442 shown in SEQ ID NO:2.

The transformant of the present invention is obtained by introducing into a host cell the expression vector comprising the DNA sequence encoding the human endothelin receptor having amino acid sequence from Glu at +27 to Ser at +442 shown in SEQ ID NO:3 and SEQ ID NO:4.

The method for producing a human endothelin receptor of the present invention comprises culturing either one of the above-mentioned transformants and recovering a produced endothelin receptor.

Thus, the invention described herein makes possible the advantage of providing a human ET-receptor, DNA sequence encoding the ET-receptor, an expression vector carrying the DNA sequence, a transformant comprising the expression vector, and a method for producing an ET-receptor from the transformant.

These and other advantages of the present invention will become apparent to those skilled in the art upon reading and understanding the following detailed description with reference to the accompanying figures.

BRIEF DESCRIPTION OF THE DRAWINGS

FIGS. 1(A–E) shows DNA coding sequence and deduced amino acid sequence of an $ET_A$-receptor according to the present invention. (SEQ ID NO:2 and SEQ ID NO:2.)

FIGS. 2(A–E) shows DNA coding sequence and deduced amino acid sequence of an $ET_B$-receptor according to the present invention. (SEQ ID NO:3 and SEQ ID NO:4.)

DESCRIPTION OF THE PREFERRED EMBODIMENTS

The inventors succeeded in isolating a human ET-receptor cDNA from a cDNA library constructed from poly(A)$^+$RNA derived from a human placenta, thereby achieving the present invention.

The present invention will be described below in order of the steps involved.

Figure 8:
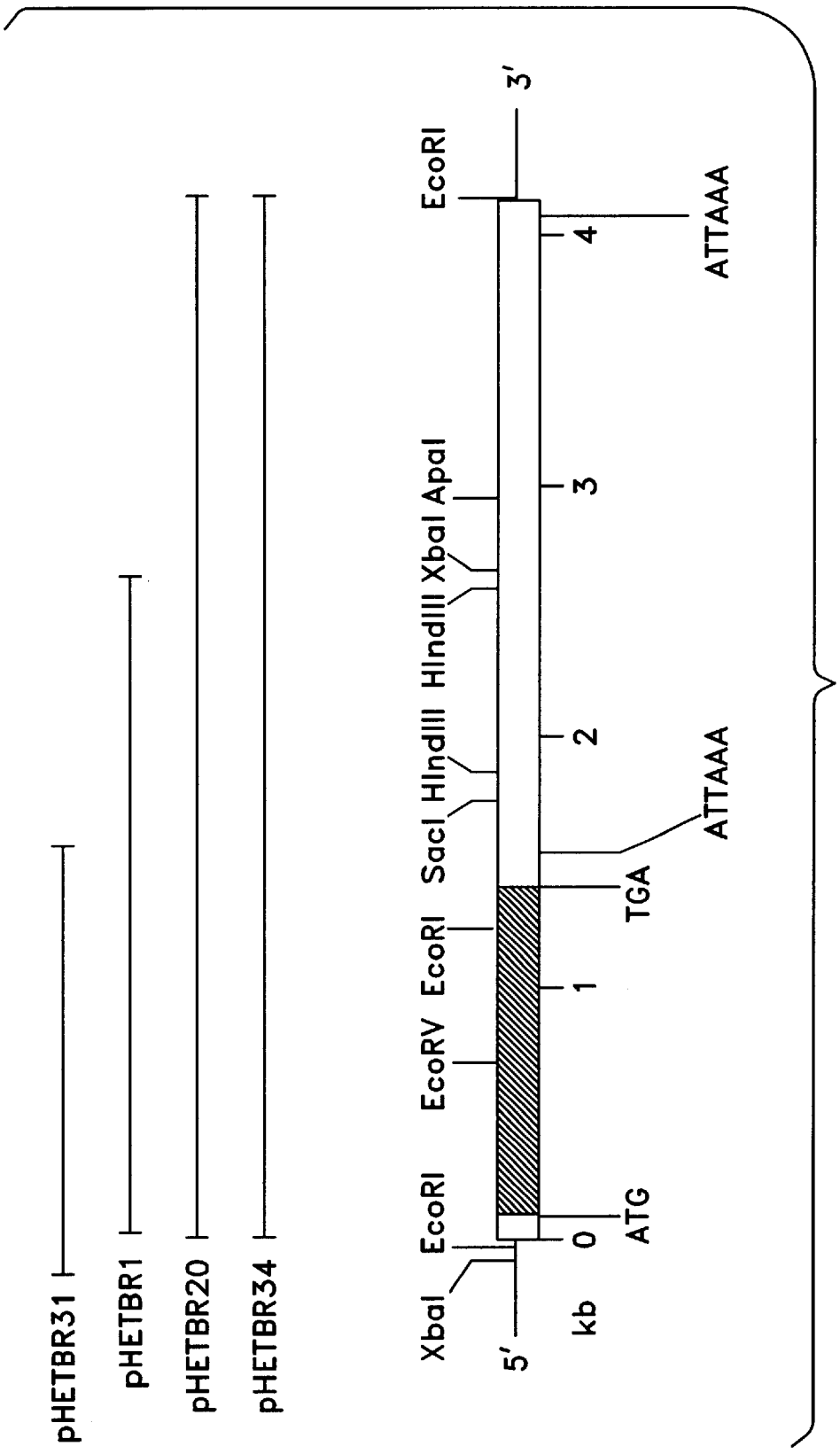
FIG. 8 is a restriction map of DNA sequence of the $ET_B$-receptor according to the present invention.

(I) Sequencing of DNA encoding a human ET-receptor:

First, cDNA prepared from poly(A)$^+$RNA derived from a human placenta, by using oligo(dT)-primer, is introduced into phage λ ZAPII to construct a cDNA library (Sambrook et al., Molecular Cloning: A Laboratory Manual, Cold Spring Harbor Laboratory, New York (1989)). Then, the cDNA library is screened with the use of DNA fragment of a known ET-receptor as a probe. For example, the cDNA library is screened by hybridizing a probe, an NcoI-EcoRI fragment (960 bp) of DNA encoding a bovine ET-1 receptor, with the cDNA library to obtain positive plasmid clone phETIR. In addition, the cDNA library is hybridized under less stringent conditions to obtain pHETBR1, pHETBR20, pHETBR31 and pHETBR34. cDNA inserts contained in these clones are cut with appropriate restriction enzymes and subcloned, after which these cDNA inserts are sequenced by the dideoxy chain termination method. The nucleic acid sequence of the human ET-receptor thus obtained from phETIR and amino acid sequence corresponding thereto are shown in SEQ ID NO:1 and SEQ ID NO:2 in a Sequence Listing. The nucleic acid sequence of the human ET-receptor thus obtained from pHETBR31 and pHETBR34 and amino acid sequence corresponding thereto are shown in SEQ ID NO:3 and SEQ ID NO:4 in Sequence Listing. A restriction map of the nucleic acid sequence in SEQ ID NO:3 and SEQ ID NO:4 is shown in FIG. 8. The positions of 3'termini of the inserts contained in pHETBR31 and pHETBR1 are respectively marked with a double line and a wave line in the sequence of FIG. 2.

The ET-receptor encoded by DNA shown in SEQ SEQ ID NO:1 and SEQ ID NO:2 is a receptor having an affinity for ET-1 and ET-2 ($ET_A$-receptor). The ET-receptor encoded by DNA shown in SEQ ID NO:2 is a receptor having an affinity (with no selectivity) for both ET-1, ET-2, and ET-3 ($ET_B$-receptor).

(1) DNA sequence of an ET-receptor ($ET_A$-receptor) from phETIR

As shown in SEQ ID NO:1 and SEQ ID NO:2 and FIG. 1, cDNA contained in the above-mentioned plasmid clone phETIR has a sequence comprising 4,105 nucleic acids. In this nucleic acid sequence, an open reading frame from A at 485 to A at 1768 are constituted, which encodes a 427-amino-acid protein with a molecular weight of 48,726. A sequence adjacent to the initiation codon of the open reading frame is quite consistent with a consensus sequence. A peptide consisting of amino acids from Met corresponding to the initiation codon to the 20th amino acid from Met may be a signal sequence. A 3'-noncoding region contains ATTTA sequence (underlined in the noncoding region of the sequences in FIG. 1), which are related with instability of mRNA. There is a potential polyadenylation signal 22-nucleotides up-stream of the poly(A)$^+$ tail (broken underlined in FIG. 1). Hydropathicity analysis of the amino acids constituting the protein encoded by this cDNA indicates that there are seven hydrophobic clusters of 22–26 residues in the protein, each being separated by hydrophilic amino acid sequences. As described above, the protein has seven transmembrane domains, and these domains have an extracellular N tail and a cytoplasmic C tail. The characteristics of this protein are consistent with those of the superfamily of G protein-coupled receptors. These seven transmembrane domains are shown as I to VII in the sequences of FIG. 1.

In the above-mentioned cDNA, there are several potential sites for post-translational modification, and these sites are identical to those of the bovine ET-1 receptor. They include two consensus sequences for N-glycosylation, Asn at 9 and 42 (shown by reverse triangles in FIG. 1); six cysteine residues present on the N terminus side of the cytoplasmic C tail (359, 363, and 365 to 368), one of which may be palmitoylated as in the $\beta_2$-adrenergic receptor; and serine residues that can be phosphorylated with serine/threonine kinases (shown by solid circles in FIG. 1).

The nucleic acid sequence of the open reading frame of cDNA obtained from phETIR is 91.2% homologous to that of bovine ET-1 receptor cDNA.

(2) DNA sequence of an ET-receptor ($ET_B$-receptor) derived from pHETBR31 and pHETBR34

As shown in SEQ ID NO:3 and SEQ ID NO:4 and FIG. 2, cDNA obtained from the above two plasmid clones has a sequence comprising 4,301 nucleic acids. In this nucleic acid sequence, an open reading frame from A at 238 to A at 1566 exists, which encodes a 442-amino acid protein with a molecular weight of 49,629. A sequence adjacent to the initiation codon of the open reading frame is quite consistent with a consensus sequence. A peptide consisting of amino acids from Met corresponding to the initiation codon to the 26th amino acid from Met may be a signal sequence. In the same way as in the DNA sequence of the ETA-receptor derived from the above-mentioned phETIR, an ATTTA sequence, seven transmembrane domains (I to VII), a polyadenylation signal, N-glycosylation sites, and serine residues that can be phosphorylated with serine/threonine kinases are shown in the sequences of FIG. 2.

Recently, Sakurai et al. cloned cDNA encoding the ET-receptor of an $ET_B$ type from a rat lung (Nature, 348, 732–735 (1990)). The amino acid sequence of $ET_B$-receptor from a rat is 88% homologous to that of the ET-receptor shown in SEQ ID NO:3 and SEQ ID NO:4 and is 51.9% homologous to that of the ET-receptor shown in SEQ ID NO:1 and SEQ ID NO:2.

The amino acid sequence of the $ET_A$-receptor shown in SEQ ID NO:1 and SEQ ID NO:2 is 55% homologous to that of the $ET_B$-receptor shown in SEQ ID NO:3 and SEQ ID NO:4. The open reading frame of the DNA sequence encoding the $ET_B$-receptor shown in SEQ ID NO:3 and SEQ ID NO:4 is 61.1% homologous to that of the bovine $ET_A$-receptor.

(II) Construction of an expression vector, a preparation of a transformant, and an expression of an ET-receptor:

cDNAs encoding the above-mentioned ET-receptors are introduced into appropriate vectors to construct expression vectors. For example, a NotI fragment of the phETIR can be introduced into CDM8 (Nature, 329, 840–842 (1987)), to obtain an expression vector CDM8-phETIR. In the same way, an XbaI fragment of pHETBR34 can be introduced into CDM8 to obtain an expression vector CDM8-pHETBR. These expression vectors can be introduced into appropriate host cells to obtain transformants. For example, a transformant capable of producing an ET-receptor can be obtained by transfecting one of the above-mentioned expression vectors into a COS-7 cell. An ET-receptor is produced by culturing the transformed COS-7 cell under normal conditions. The ET-receptor is expressed (produced) on the cell surface. The produced ET-receptor can be purified by, for example, combinations of various kinds of chromatographies.

The ET-receptor thus produced from a transformant is subjected to a binding assay by the use of known ETs and is confirmed to be an ET-receptor. In addition, it is confirmed which endothelin: ET-1, ET-2, or ET-3 the ET-receptor is specifically bound to.

Figure 3:
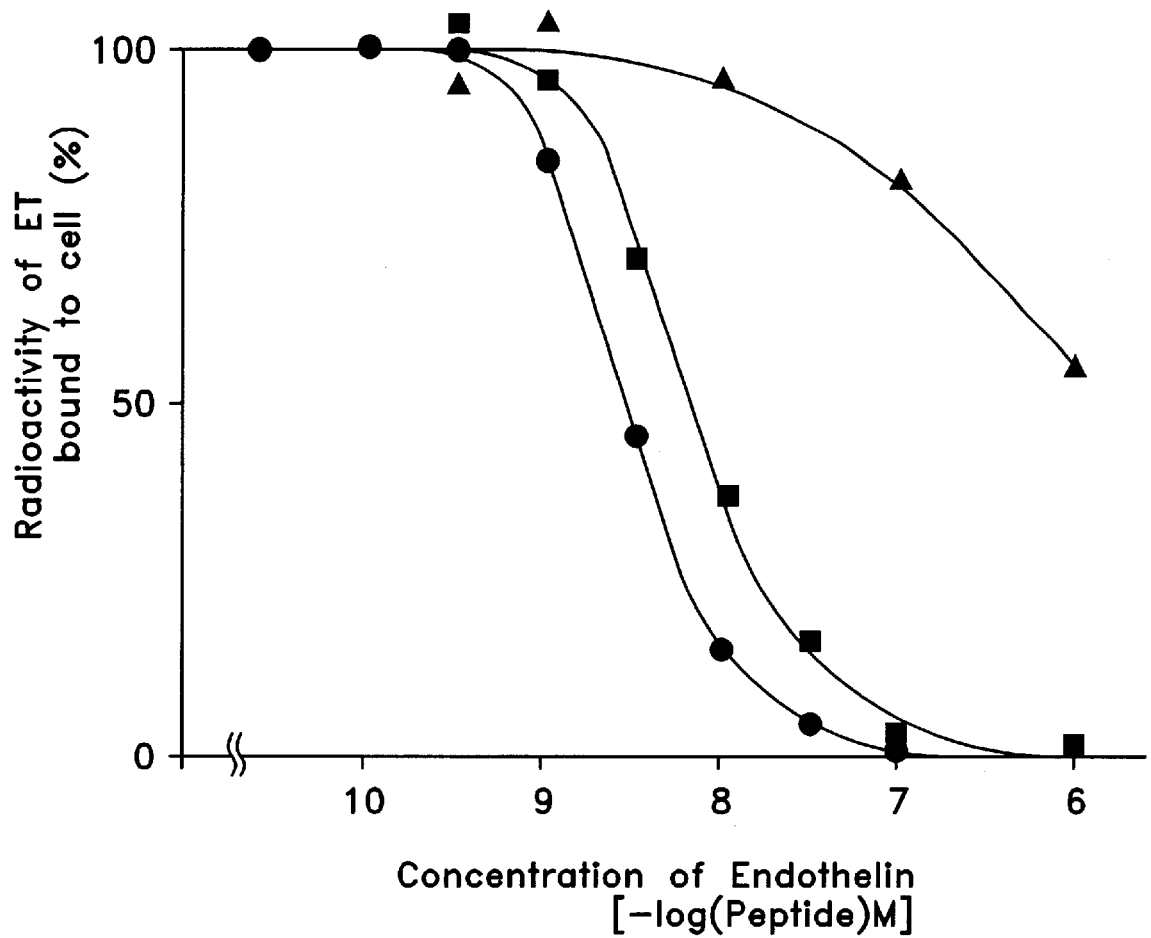
FIG. 3 is a graph showing the results of a binding assay for determining the binding properties of the $ET_A$-receptor to ET-1, ET-2, or ET-3.

For example, first, a predetermined amount of ET-receptor produced by the COS cell transformed with the CDM8-phETIR is added to a mixture of a predetermined amount of ET-1 labeled with $^{125}$I ($^{125}$I-ET-1) and unlabeled ET-1 and to allow to react. Then, the amount of labeled binding complex thus produced is measured. In FIG. 3, the amount of unlabeled ET-1 is plotted on a horizontal axis by changing the concentration thereof in the range of $10^{-10}$ to $10^{-6}$ M, and the radioactivity of an ET-ET-receptor complex (radioactivity of the ET bound to the transformed cell) is plotted on a vertical axis (represented by the symbol ●). Results obtained by performing a competitive assay using unlabeled ET-2 or ET-3 instead of unlabeled ET-1 in the same way as the above are also shown in FIG. 3 (represented by the symbols ■ (ET-2) and ▲ (ET-3)). The COS-7 cell obtained by transfecting the CDM8, which is a control plasmid, is cultured and is tested in the same way as the above. The binding amount of $^{125}$I-ET-1 is the same level as the amount of non-specific $^{125}$I-ET-1 measured in the presence of an excessive amount of unlabeled ET-1 (the results are not shown). These results indicate that the affinity of the ET-receptor from phETIR according to the present invention for the ET is ET-1 (IC$_{50}$ 3.0×10$^{-9}$ M)≧ET-2 (IC$_{50}$ 6.1×10$^{-9}$ M)>>ET-3 (IC$_{50}$ 1.0×10$^{-6}$ M or more), suggesting that this ET-receptor is the ET$_A$-receptor.

Figure 4:
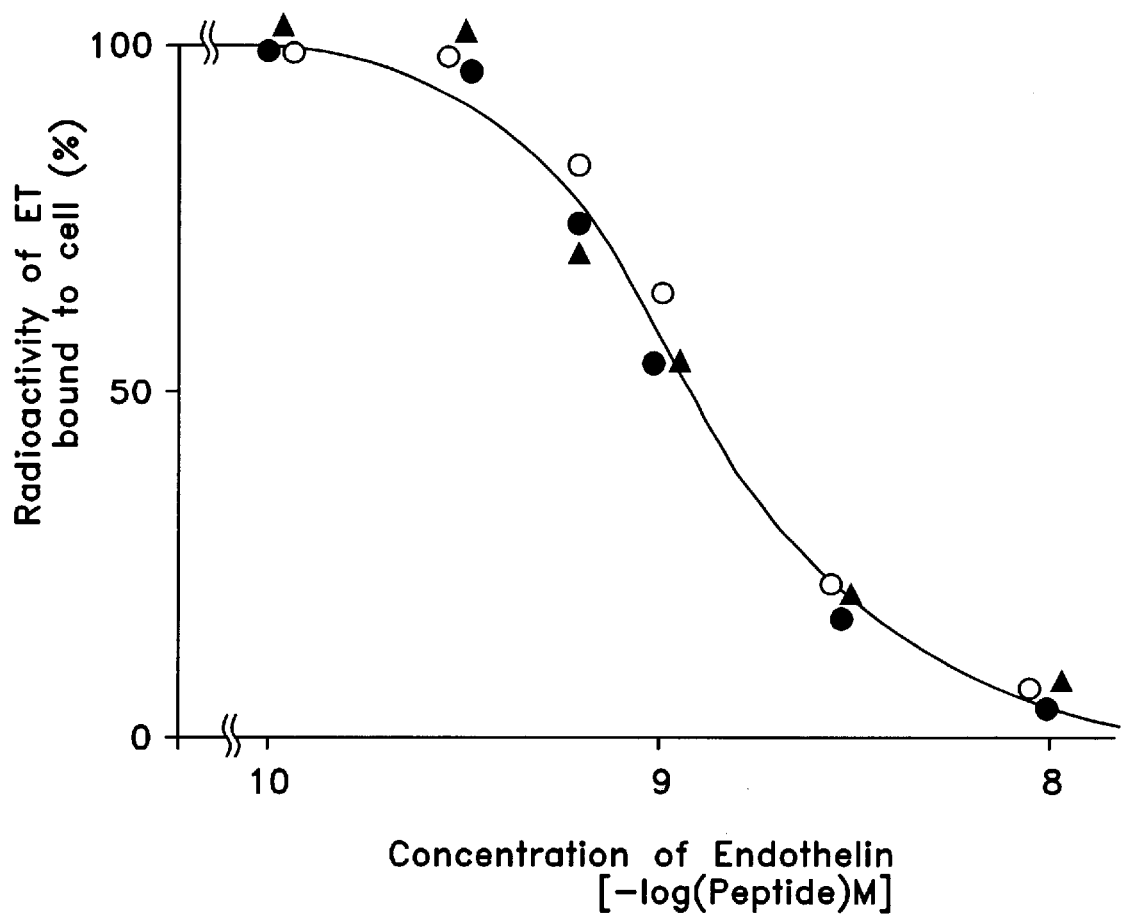
FIG. 4 is a graph showing the results of a binding assay for determining the binding properties of the $ET_B$-receptor to ET-1, ET-2, or ET-3.

The same procedure of binding assay as described above is done for the ET-receptor produced from the COS cell transformed with the CDM8-pHETBR. The results are shown in FIG. 4 (represented by the symbols ● (ET-1), ○ (ET-2), and ▲ (ET-3)). IC$_{50}$ is about 1.0×10$^{-9}$ M, suggesting that this ET-receptor is the ET$_B$-receptor.

Figure 5:
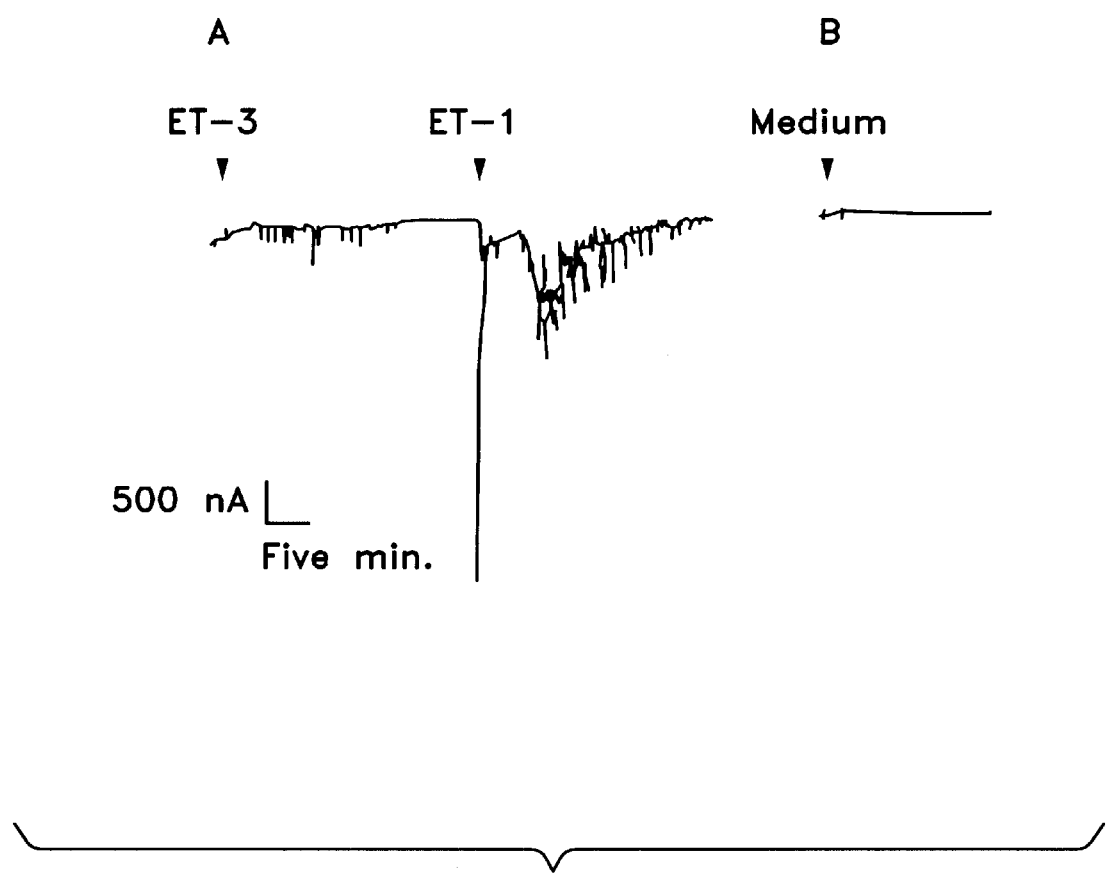
FIGS. 5(A, B) are charts recording currents, which are generated at the time that ET-1 or ET-3 (FIG. 5B), or medium alone (FIG. 5B) is applied to a Xenopus laevis oocyte injected with mRNA of the $ET_A$-receptor according to the present invention.

(III) Expression of ET-receptor mRNA in a cell:

mRNA is synthesized from the cDNA of the ET-receptor of the present invention. When the synthesized mRNA is injected into an appropriate cell, for example, an oocyte of an *Xenopus laevis*, an ET-receptor is expressed in the cell membrane. For example, mRNA is synthesized from cDNA shown in SEQ ID NO:1 obtained in item (I) with the use of T7RNA polymerase. The synthesized mRNA is injected into an oocyte of an *Xenopus laevis;* as a result, an ET$_A$-receptor is produced in the cell memblene. The production of an ET$_A$-receptor is confirmed by the following procedure. First, the membrane potential of the oocyte injected with mRNA is held at a predetermined value, and then this oocyte is brought into contact with a solution containing ET-1. If the ET$_A$-receptor of the present invention is produced, it is expressed on the cell surface, thus bound to ET-1 present outside the cell. When the ET$_A$-receptor is bound to ET-1, a current flows toward the inside of the cell. Therefore, the production of the ET-receptor of the present invention is confirmed by measuring this current. When the oocyte was brought into contact with a solution containing 10$^{-7}$ M ET-1, a current of a large value is confirmed to flow toward the inside of the cell. When the oocyte was brought into contact with a solution containing 10$^{-7}$ M ET-2 instead of ET-1, the same value of current is confirmed to flow. In contrast, when the oocyte is brought into contact with a solution containing ET-3, only a small value of current is confirmed to flow. The comparison in current values between ET-1 and ET-3 is shown in FIG. 5. From this result, the ET$_A$-receptor of the present invention has a higher affinity for ET-1 than for ET-3.

(IV) Presence of ET-receptor mRNA in various human tissues:

(1) Presence of ET$_A$-receptor mRNA

Figure 6:
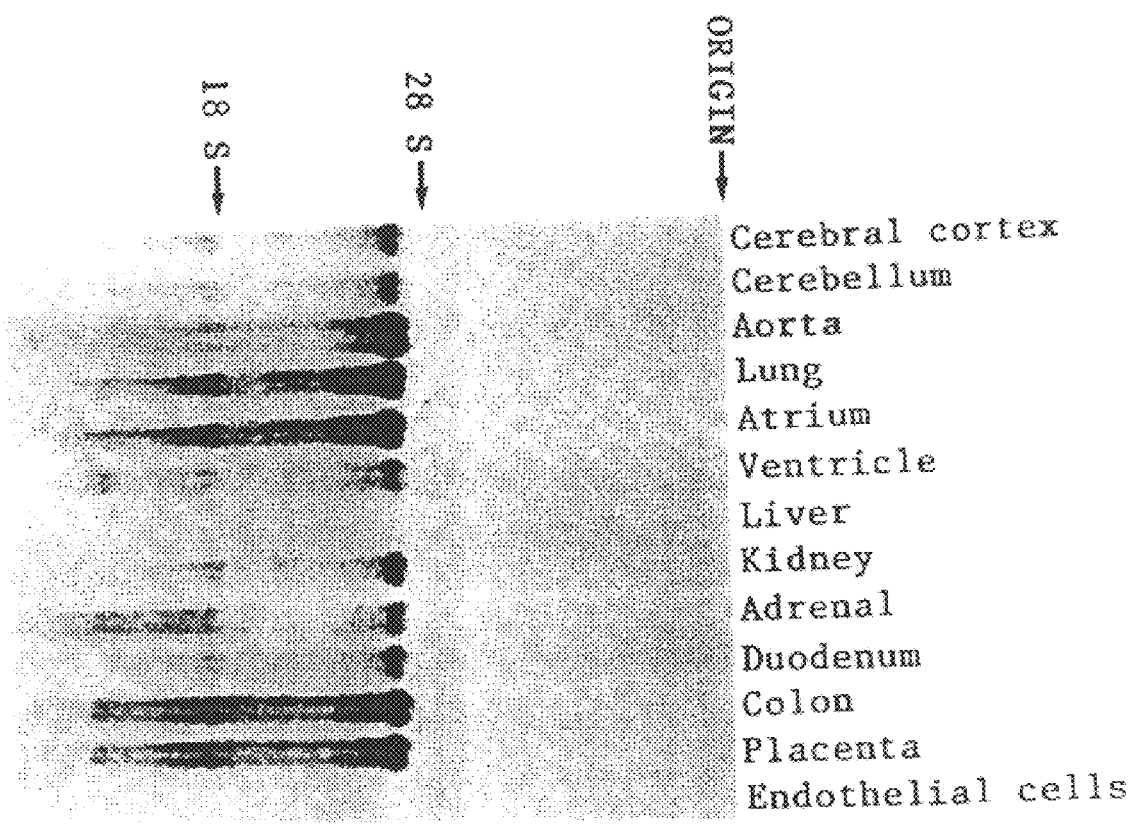
FIG. 6 is a chart of autoradiography showing the results of hybridization of mRNAs isolated from a human tissue with a cDNA fragment of the $ET_A$-receptor according to the present invention.

Northern blot hybridization analysis is conducted on mRNA isolated from various human tissues by using, as a probe, DNA fragment encoding the ET$_A$-receptor of the present invention (EcoRV-EcoRI fragment from phETIR; nucleic acids 739–1564, 826 bp) which is radio-labeled, resulting in a single positive band with a size of 4.3 kb. The results are shown in FIG. 6. The ET$_A$-receptor mRNA of the present invention is present in the aorta at the highest levels; in the lung, atrium, colon and placenta at high levels; and in the cerebral cortex, cerebellum, ventricle, kidney, adrenal and duodenum at moderate levels. A hybridized band is not found in the liver or in the cultured human umbilical vein endothelial cell.

As described above, the ET$_A$-receptor mRNA is present in the circulatory system, especially in the aorta at the highest levels. Since the ET-receptor mRNA is not present in the endthelial cell, the ET$_A$-receptor mRNA is possibly expressed in the vascular smooth muscle cell. Martin et al. describes in J. Biol. Chem. 265, 14044–14049 (1990) that ET-1 and ET-2 inhibit the binding of $^{125}$I-ET-1 to a rat A-10 vascular smooth muscle cell. This result is consistent with the experimental results that the ET$_A$-receptor of the present invention is present in the vascular smooth muscle cell. The ET$_A$-receptor of the present invention appears to be a main subtype of the ET-receptor which is expressed in the vascular smooth muscle cell.

In general, it is known that the concentration of ET-1 in plasma is increased due to various diseases such as essential hypertension, vasospastic stenocardia, acute myocardial infarction, chronic renal insufficiency, subarachnoid hemorrhage, and hypoxia. It is conceivable that ET-1 produced in and released from the endothelial cells is bound to an ET-receptor in the vascular smooth muscle cells and acts as a local regulator in maintaining vascular tonus. It is conjectured that the increase in concentration of ET-1 due to the above-mentioned diseases is caused by the collapse of balance between the amount of ET-1 bound to the ET-receptor and the amount of ET-1 released.

(2) Presence of ET$_B$-receptor mRNA

Figure 7:
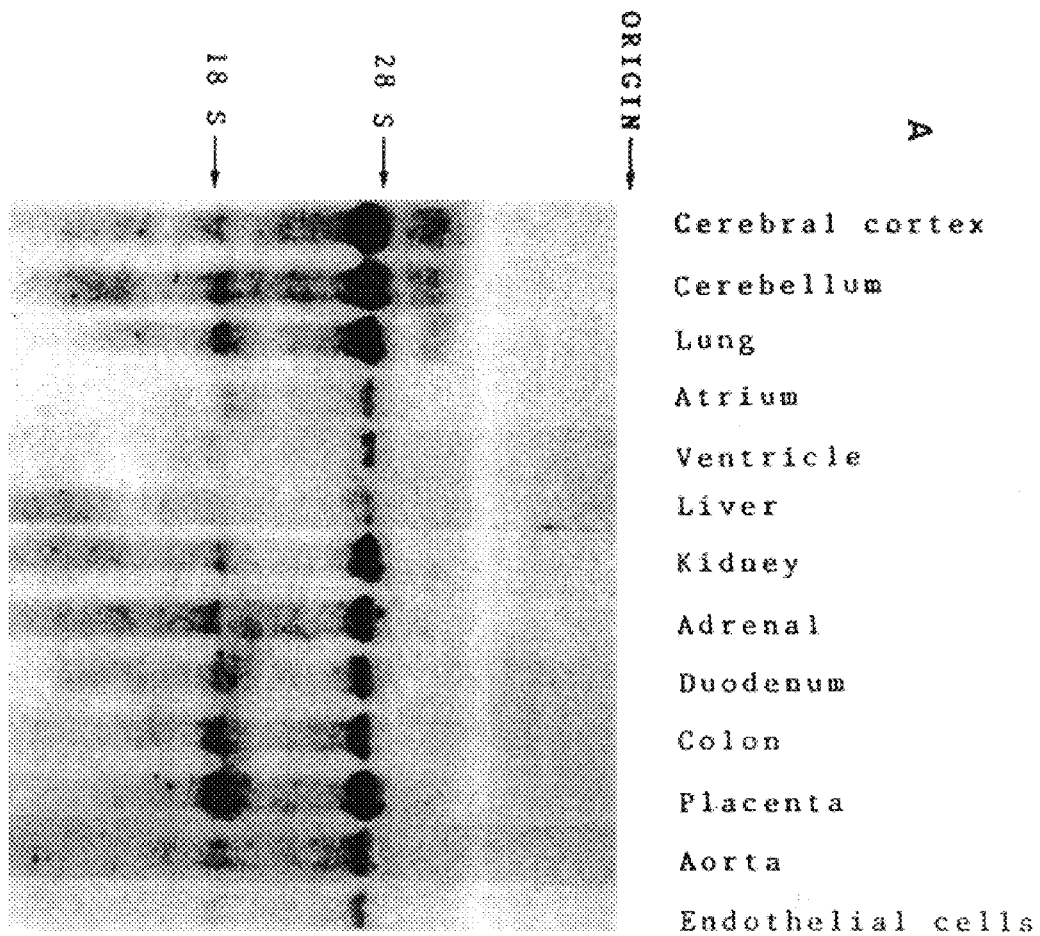
FIG. 7 is a chart of autoradiography showing the results of hybridization of mRNA isolated from a human tissue with a cDNA fragment of the $ET_B$-receptor according to the present invention.

Northern blot hybridization is conducted as described in item (1), by using a probe, 1.2 kb EcoRI fragment, which is derived from pHETBR34 and is radio-labeled, resulting in that a band with a size of 4.3 kb and a band with a size of 1.7 kb are found in various tissues as shown in FIG. 7. It is considered that the plurality of mRNAs is due to the difference in polyadenylation.

It is found that mRNAs with a size of 4.3 kb and 1.7 kb are expressed in the human cerebral cortex and cerebellum at high levels and in the placenta, lung, kidney, adrenal, colon and duodenum at moderate levels.

EXAMPLE

Hereinafter, the present invention will be described by way of illustrating examples.

(I) Sequencing of DNA encoding a human ET-receptor:

(1) Sequencing of DNA encoding a human ET$_A$-receptor

First, cDNA prepared from poly(A)$^+$RNA derived from a human placenta, by using oligo(dT)-primer, was introduced into phage λ ZAPII, to construct a cDNA library (Sambrook et al., Molecular Cloning: A laboratory Manual, Cold Spring Harbor Laboratory, New York (1989)). Approximately 1×10⁶ plaques were screened by using an NcoI-EcoRI fragment (960 bp) of DNA encoding a bovine ET-1 receptor as a probe (Nature, 348, 730–732 (1990)) in the following manner. Filters (Colony/Plaque Screen, du Pont, Wilmington, Del.) to which plaques were replicated were prehybridized for 6 hours in a solution containing 1% SDS, 1 M NaCl, 10% dextran sulfate, 200 $\mu$g/ml of yeast tRNA and 250 $\mu$g/ml of denatured salmon sperm DNA. Then the filters were hybridized at 65° C. for 18 hours with the probe (NcoI-EcoRI fragment) labeled by random-primed synthesis to the specific activity of 5×10⁸ cpm/1 $\mu$g DNA. The filters were then washed twice (30 min. per wash) in 0.2×SSC (1×SSC is 0.15 M NaCl, 15 mM sodium citrate (pH 7.0)) containing 0.1% SDS at 60° C. The resulting filters were subjected to autoradiography in which the filters were over-layered with Konica enhancing screens and Konica X-ray films (Konica, Tokyo, Japan) and left for 4 hours at −80° C. As a result, a plurality of clones which were hybridized with the probe were found. Fragments of the cDNA insert of phETIR were subcloned into the Bluescript plasmid vector (Stratagene, La Jolla, Calif.). Both strands (+−) of the cDNA insert were sequenced by the dideoxy chain termination method using Sequenase (United States Biochemical Corp., Cleveland, Ohio.). The nucleic acid sequence and a deduced amino acid sequence of the human ET-receptor obtained from phETIR are shown in SEQ ID NO:1.

(2) Sequencing of DNA encoding a human $ET_B$-receptor

In the same way as in item (1), cDNA prepared from poly(A)⁺RNA derived from a human placenta, by using oligo(dT)-primer, was introduced into phage λ ZAPII to construct a cDNA library. The approximately 1×10⁶ plaques produced were screened using the same probe used in item (1) under conditions different from those in item (1). Filters to which plaques were replicated were immersed in a solution containing 1% SDS, 1 M NaCl, 10% dextran sulfate, 200 $\mu$g/ml of yeast RNA and 250 $\mu$g/ml of denatured salmon sperm DNA, and the plaques were hybridized with the probe at 65° C. for 18 hours. The filters were then washed twice (30 min. per wash) in 0.5×SSC containing 0.1% SDS at 50° C. The resulting filters were subjected to autoradiography to detect positive clones. Three out of 20 positive clones were clones which became positive even under the highly stringent conditions of hybridization described in item (1) above, and therefore, these three clones are cDNAs of $ET_A$-receptors. Plasmids obtained from the remaining 17 clones were cut with appropriate restriction enzymes and were sequenced by the dideoxy chain termination. As a result, a cDNA sequence shown in SEQ ID NO:2 was identified from pHETBR31 and pHETBR34.

(II) Construction of an expression vector, a preparation of a transformant, and an expression of an ET-receptor:

(1) $ET_A$-receptor

A NotI fragment of the phETIR obtained in item (I) was introduced into a CDM8 (Nature, 329, 840–842 (1987)) to obtain an expression vector, CDM8-phETIR. COS-7 cells maintained in Dulbecco's modified Eagle's medium supplemented with 100 U/ml of penicillin and streptomycin and fetal bovine serum (Hazleton, Lenexa, KS) were transfected with the CDM8-phETIR, by a calcium phosphate method. Separately, the COS-7 cells were transfected with the control plasmid CDM8. Twenty micrograms of DNA per 100 mm plate were used for transfection. The transfected cells were treated with 20% glycerol for 4 hours after the transfection. Four hours after the glycerol treatment, the cells were harvested from 100 mm plates and 5×10⁴ cells/well were plated on a 24-well cell culture plate (Corning, Glass Co. Corning, N.Y.).

(2) $ET_B$-receptor

An XbaI fragment (2.7 kb) of the pHETBR34 obtained in item (I) was introduced into the CDM8 to obtain an expression vector, CDM8-pHETBR. In the same way as described in item (1), this vector was introduced into a COS-7 cell and cultured.

(III) Binding assay of an ET receptor produced from a transformant to an ET:

$^{125}$I-ET-1 ($^{125}$I-labeled ET-1) (2000 Ci/mmol) was purchased from Amersham (Buckinghamshire, UK). Unlabeled ET-1, ET-2 and ET-3 were purchased from Peptide Institute Inc. (Minoh, Japan).

(1) $ET_A$-receptor

Binding assays were performed for a transformant containing CDM8-phETIR obtained in item (II) in a 24-well cell culture plate as follows:

Confluent cells in the wells (48 hours after the glycerol treatment) were washed three times with 1 ml of Hank's balanced salt solution containing 0.1% bovine serum albumin (BSA) (binding medium). A solution containing 50 pM of $^{125}$I-ET-1 and various concentrations ($10^{-10}$ to $10^{-6}$ M) of ET-1 was added to each well. Separately, a solution containing ET-2 or ET-3 instead of ET-1 and a solution containing $^{125}$I-ET-1 alone were prepared, and were respectively added to each well. These solutions added to the wells were incubated at 37° C. for 60 min. Following three washings with 1 ml of ice-cold binding medium, the cells were dissolved in 0.5 ml of 1 N NaOH.

The cell-bound radioactivity was measured by an auto-gamma counter (Aloka, Tokyo, Japan). The total binding was calculated as follows: (the radioactivity in the absence of unlabeled ET-1, ET-2 or ET-3)−(the radioactivity in the presence of 4×10⁻⁷ M unlabeled ET-1). All measurements were conducted twice. As a result, the total binding of $^{125}$I-ET-1 was 6900 cpm (background binding in the presence of 4×10⁻⁷ M ET-1 was 150 cpm). The radioactivity in the presence of ET-1, ET-2, or ET-3 in various concentrations is represented in per cent of the total binding (6900 cpm). The results are shown in FIG. 3. It is understood from FIG. 3 that the affinity of the ET-receptor derived from the phETIR of the present invention for ETs is ET-1 ($IC_{50}$ 3.0×10⁻⁹ M)≧ET-2 ($IC_{50}$ 6.1×10⁻⁹)>>ET-3 ($IC_{50}$ 1×10⁻⁶ M or more).

(2) $ET_B$-receptor

Binding assays were performed in the same way as described in item (1) using a transformant containing the CDM8-pHETBR instead of a transformant containing the CDM8-phETIR. The results are shown in FIG. 4. In FIG. 4, ○ shows the radioactivity in the presence of ET-2; ● shows the radioactivity in the presence of ET-1; and ▲ shows the radioactivity in the presence of ET-3. It is understood from FIG. 4 that this receptor has almost the same affinity for ET-1, ET-2 and ET-3.

(IV) Expression of ET-receptor mRNA in a cell:

Approximately 10 mg of mRNA was synthesized in vitro from phETIR by using T7RNA polymerase in the presence of capping nucleotides. The mRNA thus obtained was pressure-injected into oocytes of an Xenopus laevis with a pipette. The oocytes were then incubated in sterile Barth's medium at 20° C. for 3 days. Electro-physiological measurements were performed at 20° C. In an ND96 solution (96 mM NaCl, 2 mM KCl, 1 mM $MgCl_2$, 5 mM Hepes, pH 7.6). Two glass microelectrodes filled with 4 M potassium acetate solution were inserted into an oocyte, and the membrane potential was held at −60 mV. To this oocyte, $1\times10^{-7}$ M ET-1, ET-2, or ET-3 desolved in the ND 96 solution containing 0.1% Triton X-100 and 0.1% gelatin were applied.

Twenty seconds after the application of the ET-1 solution, a large inward current was recorded from the oocytes under a holding potential at −60 mV. The chart recorded is shown in FIG. 5. A similar inward current was recorded when $1\times10^{-7}$ M ET-2 was applied (not shown). In contrast, a much smaller current was recorded when $1\times10^{-7}$ M ET-3 was applied (FIG. 5). The currents caused by the ETs were fluctuating and long-lasting, and were characteristic of $Ca^{2+}$-activated chloride currents. No currents were recorded when the medium alone (ND9 solution containing 0.1% Triton X-100 and 0.1% gelatin) was applied (FIG. 5A).

It is understood from the above results that the ET-receptor derived from the phETIR of the present invention has a higher affinity for ET-1 or ET-2 than for ET-3.

(V) Presence of ET-receptor mRNA in various human tissues:

(1) $ET_A$-receptor

Among the human tissues used herein, the cerebral cortex, cerebellum, aorta, lung, atrium, liver, kidney, adrenal, duodenum, colon and placenta were obtained from an autopsy or operation. These tissues were weighed, frozen in liquid nitrogen, and stored at −70° C. until used. Human umbilical vein endothelial cells were purchased from Colonetics Corp (San Diego, Calif.), and cultured as described in Lab. Invest. 63, 115–122 (1990).

Total RNA was isolated from each tissue by a guanidinium isocyanate/cesium chloride method. Total RNA was separated on 0.66 M formaldehyde-1% agarose gels (20 μg per lane), and transferred to a nylon membrane (Pall, Glen, Cove, N.Y.) In 20×SSC. Blots were fixed by UV crosslinking and were prehybridized at 65° C. for 12 hours in a solution containing 4×SSC, 10×Denhardt's solution (1×Denhardt's solution is 0.2% polyvinylpyrrolidone, 0.2% BSA, and 0.2% Ficoll), 0.5% SDS, and 250 μg/ml of denatured salmon sperm DNA. The blots were then hybridized at 42° C. for 4 hours in a solution containing 50% formamide, 4×SSC, 5×Denhardt's solution, 0.5% SDS, 10% dextran sulfate, 250 μg/ml of denatured salmon sperm DNA, and the radio-labeled EcoRV-EcoRI fragment of the insert of phETIR (826 bp; used as a probe). The probe was labeled by random-primed synthesis to the specific activity of $1\times10^9$ cpm/μg DNA. The blots were washed twice at room temperature (30 min. per wash): once at 60° C. In a solution containing 2×SSC and 0.1% SDS (30 min. per wash) and twice at 60° C. In a solution containing 0.1×SSC and 0.1% SDS (15 min. per wash).

The resulting blots were subjected to autoradiography in which filters carrying blots were overlayered with Konica enhancing screens and Kodak X-Omat AR film (Kodak, Corp. Rochester, N.Y.) and left for 3 days at −70° C. The results are shown in FIG. 6. A single band with a size of 4.3 kb is located in various tissues, suggesting that mRNAs of the ET-receptor of the present invention are present in various tissues. In particular, the mRNAs are present in the aorta at the highest levels; in the lung, atrium, colon, and placenta at high levels; and in the cerebral cortex, cerebellum, ventricle, kidney, adrenal, and duodenum at moderate levels. A hybridized band is not found in the liver and in the cultured human umbilical vein endothelial cell.

(2) $ET_B$-receptor

Autoradiography was performed in the same way as described in item (1) above, except that the radio-labeled EcoRI fragment (1.2 kb) of the insert of pHETBR34 was used as a probe instead of the radio-labeled EcoRV-EcoRI fragment of the insert of pHETIR. The results are shown in FIG. 7. As shown in FIG. 7, bands with a size of about 4.3 kb and 1.7 kb are located. It is understood that the $ET_B$-receptor mRNA is present in the cerebral cortex and cerebellum at high levels. In addition, unlike the $ET_A$-receptor, the $ET_B$-receptor mRNA is present in the umbilical vein endothelial cell.

As described above, according to the present invention, a novel human endothelin receptor, DNA sequence encoding the receptor, an expression vector having the DNA sequence, a transformant comprising the expression vector, and a method for producing a human endothelin receptor from the transformant are provided. The receptor shown in SEQ ID NO:1 and SEQ ID NO:2 is an $ET_A$-receptor which has an affinity for ET-1 and ET-2, especially the affinity for ET-1 being stronger. The receptor shown in SEQ ID NO:3 and SEQ ID NO:4 is an $ET_B$-recetor which has an affinity for ET-1, ET-2 and ET-3 (with no selectivity). Thus, it is the first time that both an $ET_A$-receptor and an $ET_B$-receptor are found in a specific mammal. The ET-receptors obtained are useful as an agent for measuring the amount of ET or useful in screening for an antagonist of the ET-receptors so as to study agents for the circulatory system.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

The following specific sequence information and descriptions are provided in order to comply with the formal requirements of the submission of sequence data to the United States Patent and Trademark Office and are not intended to limit the scope of what the inventors regard as their invention. Variations in sequences which become apparent to those skilled in the art upon review of this disclosure and which are encompassed by the attached claims are intended to be within the scope of the present invention. Further, it should be noted that efforts have been made to insure accuracy with respect to the specific sequences and characteristic description information describing such sequences, but some experimental error and/or deviation should be accounted for.

What is claimed is:

1. An isolated and purified DNA molecule encoding human endothelin receptor having an affinity for endothelins 1 and 2, comprising a nucleic acid sequence from G at 545 to C at 1765 shown in SEQ ID NO:1.

2. A DNA sequence according to claim 1, comprising a nucleic acid sequence from A at 485 to C at 1765 shown in SEQ ID NO:1.

3. A DNA sequence according to claim 1, comprising a nucleic acid sequence from G at 1 to T at 4105 shown in SEQ ID NO:1.

4. An expression vector comprising the DNA sequence according to claim 1.

5. An expression vector according to claim 4, which is CDM8-phETIR.

6. A transformant obtained by introducing the expression vector according to claim 4 into a host cell.

7. A transformant according to claim 6, wherein the host cell is a COS-7 cell.

8. A method for producing a human endothelin receptor comprising culturing the transformant according to claim 6 and recovering a produced endothelin receptor.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
    (A) LENGTH: 4105 base pairs
    (B) TYPE: nucleic acid
    (C) STRANDEDNESS: single
    (D) TOPOLOGY: linear (ix) FEATURE:
    (A) NAME/KEY: CDS
    (B) LOCATION: 485..1768

(ix) FEATURE:
    (A) NAME/KEY: mat_peptide
    (B) LOCATION: 545

(xi) SEQUENCE DESCRIPTION: SEQ ID NO:1:

```
GAATTCGCGG CCGCCTCTTG CGGTCCCAGA GTGGAGTGGA AGGTCTGGAG CTTTGGGAGG      60

AGACGGGGAG GACAGACTGG AGGCGTGTTC CTCCGGAGTT TTCTTTTTCG TGCGAGCCCT     120

CGCGCGCGCG TACAGTCATC CCGCTGGTCT GACGATTGTG GAGAGGCGGT GGAGAGGCTT     180

CATCCATCCC ACCCGGTCGT CGCCGGGGAT TGGGGTCCCA GCGACACCTC CCCGGGAGAA     240

GCAGTGCCCA GGAAGTTTTC TGAAGCCGGG GAAGCTGTGC AGCCGAAGCC GCCGCCGCGC     300

CGGAGCCCGG GACACCGGCC ACCCTCCGCG CCACCCACCC TCGCTTTCTC CGGCTTCCTC     360

TGGCCCAGGC GCCGCGCGGA CCCGGCAGCT GTCTGCGCAC GCCGAGCTCC ACGGTGAAAA     420

AAAAAGTGAA GGTGTAAAAG CAGCACAAGT GCAATAAGAG ATATTTCCTC AAATTTGCCT     480
```

```
CAAG ATG GAA ACC CTT TGC CTC AGG GCA TCC TTT TGG CTG GCA CTG GTT     529
     Met Glu Thr Leu Cys Leu Arg Ala Ser Phe Trp Leu Ala Leu Val
         -20             -15                 -10

GGA TGT GTA ATC AGT GAT AAT CCT GAG AGA TAC AGC ACA AAT CTA AGC     577
Gly Cys Val Ile Ser Asp Asn Pro Glu Arg Tyr Ser Thr Asn Leu Ser
 -5                1               5                      10

AAT CAT GTG GAT GAT TTC ACC ACT TTT CGT GGC ACA GAG CTC AGC TTC     625
Asn His Val Asp Asp Phe Thr Thr Phe Arg Gly Thr Glu Leu Ser Phe
            15                  20                  25

CTG GTT ACC ACT CAT CAA CCC ACT AAT TTG GTC CTA CCC AGC AAT GGC     673
Leu Val Thr Thr His Gln Pro Thr Asn Leu Val Leu Pro Ser Asn Gly
        30                  35                  40

TCA ATG CAC AAC TAT TGC CCA CAG CAG ACT AAA ATT ACT TCA GCT TTC     721
Ser Met His Asn Tyr Cys Pro Gln Gln Thr Lys Ile Thr Ser Ala Phe
    45                  50                  55

AAA TAC ATT AAC ACT GTG ATA TCT TGT ACT ATT TTC ATC GTG GGA ATG     769
Lys Tyr Ile Asn Thr Val Ile Ser Cys Thr Ile Phe Ile Val Gly Met
60                  65                  70                  75

GTG GGG AAT GCA ACT CTG CTC AGG ATC ATT TAC CAG AAC AAA TGT ATG     817
Val Gly Asn Ala Thr Leu Leu Arg Ile Ile Tyr Gln Asn Lys Cys Met
                80                  85                  90

AGG AAT GGC CCC AAC GCG CTG ATA GCC AGT CTT GCC CTT GGA GAC CTT     865
Arg Asn Gly Pro Asn Ala Leu Ile Ala Ser Leu Ala Leu Gly Asp Leu
            95                  100                 105

ATC TAT GTG GTC ATT GAT CTC CCT ATC AAT GTA TTT AAG CTG CTG GCT     913
Ile Tyr Val Val Ile Asp Leu Pro Ile Asn Val Phe Lys Leu Leu Ala
        110                 115                 120

GGG CGC TGG CCT TTT GAT CAC AAT GAC TTT GGC GTA TTT CTT TGC AAG     961
Gly Arg Trp Pro Phe Asp His Asn Asp Phe Gly Val Phe Leu Cys Lys
    125                 130                 135

CTG TTC CCC TTT TTG CAG AAG TCC TCG GTG GGG ATC ACC GTC CTC AAC    1009
Leu Phe Pro Phe Leu Gln Lys Ser Ser Val Gly Ile Thr Val Leu Asn
140                 145                 150                 155

CTC TGC GCT CTT AGT GTT GAC AGG TAC AGA GCA GTT GCC TCC TGG AGT    1057
Leu Cys Ala Leu Ser Val Asp Arg Tyr Arg Ala Val Ala Ser Trp Ser
```

-continued

```
                 160                 165                 170
CGT GTT CAG GGA ATT GGG ATT CCT TTG GTA ACT GCC ATT GAA ATT GTC    1105
Arg Val Gln Gly Ile Gly Ile Pro Leu Val Thr Ala Ile Glu Ile Val
            175                 180                 185

TCC ATC TGG ATC CTG TCC TTT ATC CTG GCC ATT CCT GAA GCG ATT GGC    1153
Ser Ile Trp Ile Leu Ser Phe Ile Leu Ala Ile Pro Glu Ala Ile Gly
            190                 195                 200

TTC GTC ATG GTA CCC TTT GAA TAT AGG GGT GAA CAG CAT AAA ACC TGT    1201
Phe Val Met Val Pro Phe Glu Tyr Arg Gly Glu Gln His Lys Thr Cys
            205                 210                 215

ATG CTC AAT GCC ACA TCA AAA TTC ATG GAG TTC TAC CAA GAT GTA AAG    1249
Met Leu Asn Ala Thr Ser Lys Phe Met Glu Phe Tyr Gln Asp Val Lys
220                 225                 230                 235

GAC TGG TGG CTC TTC GGG TTC TAT TTC TGT ATG CCC TTG GTG TGC ACT    1297
Asp Trp Trp Leu Phe Gly Phe Tyr Phe Cys Met Pro Leu Val Cys Thr
                240                 245                 250

GCG ATC TTC TAC ACC CTC ATG ACT TGT GAG ATG TTG AAC AGA AGG AAT    1345
Ala Ile Phe Tyr Thr Leu Met Thr Cys Glu Met Leu Asn Arg Arg Asn
                255                 260                 265

GGC AGC TTG AGA ATT GCC CTC AGT GAA CAT CTT AAG CAG CGT CGA GAA    1393
Gly Ser Leu Arg Ile Ala Leu Ser Glu His Leu Lys Gln Arg Arg Glu
            270                 275                 280

GTG GCA AAA ACA GTT TTC TGC TTG GTT GTA ATT TTT GCT CTT TGC TGG    1441
Val Ala Lys Thr Val Phe Cys Leu Val Val Ile Phe Ala Leu Cys Trp
            285                 290                 295

TTC CCT CTT CAC TTA AGC CGT ATA TTG AAG AAA ACT GTG TAT AAC GAA    1489
Phe Pro Leu His Leu Ser Arg Ile Leu Lys Lys Thr Val Tyr Asn Glu
300                 305                 310                 315

ATG GAC AAG AAC CGA TGT GAA TTA CTT AGT TTC TTA CTC CTC ATG GAT    1537
Met Asp Lys Asn Arg Cys Glu Leu Leu Ser Phe Leu Leu Leu Met Asp
                320                 325                 330

TAC ATC GGT ATT AAC TTG GCA ACC ATG AAT TCA TGT ATA AAC CCC ATA    1585
Tyr Ile Gly Ile Asn Leu Ala Thr Met Asn Ser Cys Ile Asn Pro Ile
                335                 340                 345

GCT CTG TAT TTT GTG AGC AAG AAA TTT AAA AAT TGT TTC CAG TCA TGC    1633
Ala Leu Tyr Phe Val Ser Lys Lys Phe Lys Asn Cys Phe Gln Ser Cys
            350                 355                 360

CTC TGC TGC TGT TAC CAG TCC AAA AGT CTG ATG ACC TCG GTC CCC        1681
Leu Cys Cys Cys Tyr Gln Ser Lys Ser Leu Met Thr Ser Val Pro
            365                 370                 375

ATG AAC GGA ACA AGC ATC CAG TGG AAG AAC CAC GAT CAA AAC AAC CAC    1729
Met Asn Gly Thr Ser Ile Gln Trp Lys Asn His Asp Gln Asn Asn His
380                 385                 390                 395

AAC ACA GAC CGG AGC AGC CAT AAG GAC AGC ATG AAC TGACCACCCT         1775
Asn Thr Asp Arg Ser Ser His Lys Asp Ser Met Asn
                400                 405

TAGAAGCACT CCTCGGTACT CCCATAATCC TCTCGGAGAA AAAAATCACA AGGCAACTGT  1835

GACTCCGGGA ATCTCTTCTC TGATCCTTCT TCCTTAATTC ACTCCCACAC CCAAGAAGAA  1895

ATGCTTTCCA AAACCGCAAG GTAGACTGGT TTATCCACCC ACAACATCTA CGAATCGTAC  1955

TTCTTTAATT GATCTAATTT ACATATTCTG CGTGTTGTAT TCAGCACTAA AAAATGGTGG  2015

GAGCTGGGGG AGAATGAAGA CTGTTAAATG AAACCAGAAG GATATTTACT ACTTTTGCAT  2075

GAAAATAGAG CTTTCAAGTA CATGGCTAGC TTTTATGGCA GTTCTGGTGA ATGTTCAATG  2135

GGAACTGGTC ACCATGAAAC TTTAGAGATT AACGACAAGA TTTTCTACTT TTTTTAAGTG  2195

ATTTTTTGTC CTTCAGCCAA ACACAATATG GGCTCAGGTC ACTTTTATTT GAAATGTCAT  2255

TTGGTGCCAG TATTTTTTAA CTGCATAATA GCCTAACATG ATTATTTGAA CTTATTTACA  2315
```

-continued

```
CATAGTTTGA AAAAAAAAAG ACAAAAATAG TATTCAGGTG AGCAATTAGA TTAGTATTTT      2375

CCACGTCACT ATTTATTTTT TTAAAACACA AATTCTAAAG CTACAACAAA TACTACAGGC      2435

CCTTAAAGCA CAGTCTGATG ACACATTTGG CAGTTTAATA GATGTTACTC AAAGAATTTT      2495

TTAAGAACTG TATTTATTT TTTAAATGGT GTTTTATTAC AAGGGACCTT GAACATGTTT      2555

TGTATGTTAA ATTCAAAAGT AATGCTTCAA TCAGATAGTT CTTTTTCACA AGTTCAATAC      2615

TGTTTTTCAT GTAAATTTTG TATGAAAAAT CAATGTCAAG TACCAAAATG TTAATGTATG      2675

TGTCATTTAA CTCTGCCTGA GACTTTCAGT GCACTGTATA TAGAAGTCTA AAACACACCT      2735

AAGAGAAAAA GATCGAATTT TTCAGATGAT TCGGAAATTT TCATTCAGGT ATTTGTAATA      2795

GTGACATATA TATGTATATA CATATCACCT CCTATTCTCT TAATTTTTGT TAAAATGTTA      2855

ACTGGCAGTA AGTCTTTTTT GATCATTCCC TTTTCCATAT AGGAAACATA ATTTTGAAGT      2915

GGCCAGATGA GTTTATCATG TCAGTGAAAA ATAATTACCC ACAAATGCCA CCAGTAACTT      2975

AACGATTCTT CACTTCTTGG GGTTTTCAGT ATGAACCTAA CTCCCCACCC CAACATCTCC      3035

CTCCCACATT GTCACCATTT CAAAGGGCCC ACAGTGACTT TGCTGGGCA TTTTCCCAGA      3095

TGTTTACAGA CTGTGAGTAC AGCAGAAAAT CTTTTACTAG TGTGTGTGTG TATATATATA      3155

AACAATTGTA AATTTCTTTT AGCCCATTTT TCTAGACTGT CTCTGTGGAA TATATTTGTG      3215

TGTGTGATAT ATGCATGTGT GTGATGGTAT GTATGGATTT AATCTAATCT AATAATTGTG      3275

CCCCGCAGTT GTGCCAAAGT GCATAGTCTG AGCTAAAATC TAGGTGATTG TTCATCATGA      3335

CAACCTGCCT CAGTCCATTT TAACCTGTAG CAACCTTCTG CATTCATAAA TCTTGTAATC      3395

ATGTTACCAT TACAAATGGG ATATAAGAGG CAGCGTGAAA GCAGATGAGC TGTGGACTAG      3455

CAATATAGGG TTTTGTTTGG TTGGTTGGTT TGATAAAGCA GTATTTGGGG TCATATTGTT      3515

TCCTGTGCTG GAGCAAAAGT CATTACACTT TGAAGTATTA TATTGTTCTT ATCCTCAATT      3575

CAATGTGGTG ATGAAATTGC CAGGTTGTCT GATATTTCTT TCAGACTTCG CCAGACAGAT      3635

TGCTGATAAT AAATTAGGTA AGATAATTTG TTGGGCCATA TTTTAGGACA GGTAAAATAA      3695

CATCAGGTTC CAGTTGCTTG AATTGCAAGG CTAAGAAGTA CTGCCCTTTT GTGTGTTAGC      3755

AGTCAAATCT ATTATTCCAC TGGCGCATCA TATGCAGTGA TATATGCCTA TAATATAAGC      3815

CATAGGTTCA CACCATTTTG TTTAGACAAT TGTCTTTTTT TCAAGATGCT TTGTTTCTTT      3875

CATATGAAAA AAATGCATTT TATAAATTCA GAAAGTCATA GATTTCTGAA GGCGTCAACG      3935

TGCATTTTAT TTATGGACTG GTAAGTAACT GTGGTTTACT AGCAGGAATA TTTCCAATTT      3995

CTACCTTTAC TACATCTTTT CAACAAGTAA CTTTGTAGAA ATGAGCCAGA AGCCAAGGCC      4055

CTGAGTTGGC AGTGGCCCAT AAGTGTAAAA TAAAAGTTTA CAGAAACCTT               4105
```

(2) INFORMATION FOR SEQ ID NO:2:

(i) SEQUENCE CHARACTERISTICS:
        (A) LENGTH: 427 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Thr Leu Cys Leu Arg Ala Ser Phe Trp Leu Ala Leu Val Gly
-20             -15                 -10                 -5

Cys Val Ile Ser Asp Asn Pro Glu Arg Tyr Ser Thr Asn Leu Ser Asn
                1               5                   10
```

-continued

His Val Asp Asp Phe Thr Thr Phe Arg Gly Thr Glu Leu Ser Phe Leu
        15                  20                  25

Val Thr Thr His Gln Pro Thr Asn Leu Val Leu Pro Ser Asn Gly Ser
        30                  35                  40

Met His Asn Tyr Cys Pro Gln Gln Thr Lys Ile Thr Ser Ala Phe Lys
        45                  50                  55                  60

Tyr Ile Asn Thr Val Ile Ser Cys Thr Ile Phe Ile Val Gly Met Val
                    65                  70                  75

Gly Asn Ala Thr Leu Leu Arg Ile Ile Tyr Gln Asn Lys Cys Met Arg
                80                  85                  90

Asn Gly Pro Asn Ala Leu Ile Ala Ser Leu Ala Leu Gly Asp Leu Ile
            95                  100                 105

Tyr Val Val Ile Asp Leu Pro Ile Asn Val Phe Lys Leu Leu Ala Gly
        110                 115                 120

Arg Trp Pro Phe Asp His Asn Asp Phe Gly Val Phe Leu Cys Lys Leu
125                 130                 135                 140

Phe Pro Phe Leu Gln Lys Ser Ser Val Gly Ile Thr Val Leu Asn Leu
                145                 150                 155

Cys Ala Leu Ser Val Asp Arg Tyr Arg Ala Val Ala Ser Trp Ser Arg
                160                 165                 170

Val Gln Gly Ile Gly Ile Pro Leu Val Thr Ala Ile Glu Ile Val Ser
        175                 180                 185

Ile Trp Ile Leu Ser Phe Ile Leu Ala Ile Pro Glu Ala Ile Gly Phe
        190                 195                 200

Val Met Val Pro Phe Glu Tyr Arg Gly Glu Gln His Lys Thr Cys Met
205                 210                 215                 220

Leu Asn Ala Thr Ser Lys Phe Met Glu Phe Tyr Gln Asp Val Lys Asp
                225                 230                 235

Trp Trp Leu Phe Gly Phe Tyr Phe Cys Met Pro Leu Val Cys Thr Ala
                240                 245                 250

Ile Phe Tyr Thr Leu Met Thr Cys Glu Met Leu Asn Arg Arg Asn Gly
        255                 260                 265

Ser Leu Arg Ile Ala Leu Ser Glu His Leu Lys Gln Arg Arg Glu Val
        270                 275                 280

Ala Lys Thr Val Phe Cys Leu Val Val Ile Phe Ala Leu Cys Trp Phe
285                 290                 295                 300

Pro Leu His Leu Ser Arg Ile Leu Lys Lys Thr Val Tyr Asn Glu Met
                305                 310                 315

Asp Lys Asn Arg Cys Glu Leu Leu Ser Phe Leu Leu Leu Met Asp Tyr
                320                 325                 330

Ile Gly Ile Asn Leu Ala Thr Met Asn Ser Cys Ile Asn Pro Ile Ala
        335                 340                 345

Leu Tyr Phe Val Ser Lys Lys Phe Lys Asn Cys Phe Gln Ser Cys Leu
        350                 355                 360

Cys Cys Cys Cys Tyr Gln Ser Lys Ser Leu Met Thr Ser Val Pro Met
365                 370                 375                 380

Asn Gly Thr Ser Ile Gln Trp Lys Asn His Asp Gln Asn Asn His Asn
                385                 390                 395

Thr Asp Arg Ser Ser His Lys Asp Ser Met Asn
                400                 405

(2) INFORMATION FOR SEQ ID NO:3:

(i) SEQUENCE CHARACTERISTICS:

-continued (A) LENGTH: 4301 base pairs
(B) TYPE: nucleic acid
(C) STRANDEDNESS: single
(D) TOPOLOGY: linear (ix) FEATURE:
(A) NAME/KEY: CDS
(B) LOCATION: 238..1566

(xi) SEQUENCE DESCRIPTION: SEQ ID NO:3:

```
GAGACATTCC GGTGGGGGAC TCTGGCCAGC CCGAGCAACG TGGATCCTGA GAGCACTCCC      60

AGGTAGGCAT TTGCCCCGGT GGGACGCCTT GCCAGAGCAG TGTGTGGCAG GCCCCCGTGG     120

AGGATCAACA CAGTGGCTGA ACACTGGGAA GGAACTGGTA CTTGGAGTCT GGACATCTGA     180

AACTTGGCTC TGAAACTGCG GAGCGGCCAC CGGACGCCTT CTGGAGCAGG TAGCAGC       237

ATG CAG CCG CCT CCA AGT CTG TGC GGA CGC GCC CTG GTT GCG CTG GTT     285
Met Gln Pro Pro Pro Ser Leu Cys Gly Arg Ala Leu Val Ala Leu Val
  1               5                  10                 15

CTT GCC TGC GGC CTG TCG CGG ATC TGG GGA GAG GAG AGA GGC TTC CCG     333
Leu Ala Cys Gly Leu Ser Arg Ile Trp Gly Glu Glu Arg Gly Phe Pro
            20                  25                  30

CCT GAC AGG GCC ACT CCG CTT TTG CAA ACC GCA GAG ATA ATG ACG CCA     381
Pro Asp Arg Ala Thr Pro Leu Leu Gln Thr Ala Glu Ile Met Thr Pro
        35                  40                  45

CCC ACT AAG ACC TTA TGG CCC AAG GGT TCC AAC GCC AGT CTG GCG CGG     429
Pro Thr Lys Thr Leu Trp Pro Lys Gly Ser Asn Ala Ser Leu Ala Arg
    50                  55                  60

TCG TTG GCA CCT GCG GAG GTG CCT AAA GGA GAC AGG ACG GCA GGA TCT     477
Ser Leu Ala Pro Ala Glu Val Pro Lys Gly Asp Arg Thr Ala Gly Ser
 65                  70                  75                  80

CCG CCA CGC ACC ATC TCC CCT CCC CCG TGC CAA GGA CCC ATC GAG ATC     525
Pro Pro Arg Thr Ile Ser Pro Pro Pro Cys Gln Gly Pro Ile Glu Ile
                85                  90                  95

AAG GAG ACT TTC AAA TAC ATC AAC ACG GTT GTG TCC TGC CTT GTG TTC     573
Lys Glu Thr Phe Lys Tyr Ile Asn Thr Val Val Ser Cys Leu Val Phe
            100                 105                 110

GTG CTG GGG ATC ATC GGG AAC TCC ACA CTT CTG AGA ATT ATC TAC AAG     621
Val Leu Gly Ile Ile Gly Asn Ser Thr Leu Leu Arg Ile Ile Tyr Lys
        115                 120                 125

AAC AAG TGC ATG CGA AAC GGT CCC AAT ATC TTG ATC GCC AGC TTG GCT     669
Asn Lys Cys Met Arg Asn Gly Pro Asn Ile Leu Ile Ala Ser Leu Ala
    130                 135                 140

CTG GGA GAC CTG CTG CAC ATC GTC ATT GAC ATC CCT ATC AAT GTC TAC     717
Leu Gly Asp Leu Leu His Ile Val Ile Asp Ile Pro Ile Asn Val Tyr
145                 150                 155                 160

AAG CTG CTG GCA GAG GAC TGG CCA TTT GGA GCT GAG ATG TGT AAG CTG     765
Lys Leu Leu Ala Glu Asp Trp Pro Phe Gly Ala Glu Met Cys Lys Leu
                165                 170                 175

GTG CCT TTC ATA CAG AAA GCC TCC GTG GGA ATC ACT GTG CTG AGT CTA     813
Val Pro Phe Ile Gln Lys Ala Ser Val Gly Ile Thr Val Leu Ser Leu
            180                 185                 190

TGT GCT CTG AGT ATT GAC AGA TAT CGA GCT GTT GCT TCT TGG AGT AGA     861
Cys Ala Leu Ser Ile Asp Arg Tyr Arg Ala Val Ala Ser Trp Ser Arg
        195                 200                 205

ATT AAA GGA ATT GGG GTT CCA AAA TGG ACA GCA GTA GAA ATT GTT TTG     909
Ile Lys Gly Ile Gly Val Pro Lys Trp Thr Ala Val Glu Ile Val Leu
    210                 215                 220

ATT TGG GTG GTC TCT GTG GTT CTG GCT GTC CCT GAA GCC ATA GGT TTT     957
Ile Trp Val Val Ser Val Val Leu Ala Val Pro Glu Ala Ile Gly Phe
225                 230                 235                 240
```

-continued

```
GAT ATA ATT ACG ATG GAC TAC AAA GGA AGT TAT CTG CGA ATC TGC TTG      1005
Asp Ile Ile Thr Met Asp Tyr Lys Gly Ser Tyr Leu Arg Ile Cys Leu
            245                 250                 255

CTT CAT CCC GTT CAG AAG ACA GCT TTC ATG CAG TTT TAC AAG ACA GCA      1053
Leu His Pro Val Gln Lys Thr Ala Phe Met Gln Phe Tyr Lys Thr Ala
            260                 265                 270

AAA GAT TGG TGG CTG TTC AGT TTC TAT TTC TGC TTG CCA TTG GCC ATC      1101
Lys Asp Trp Trp Leu Phe Ser Phe Tyr Phe Cys Leu Pro Leu Ala Ile
            275                 280                 285

ACT GCA TTT TTT TAT ACA CTA ATG ACC TGT GAA ATG TTG AGA AAG AAA      1149
Thr Ala Phe Phe Tyr Thr Leu Met Thr Cys Glu Met Leu Arg Lys Lys
            290                 295                 300

AGT GGC ATG CAG ATT GCT TTA AAT GAT CAC CTA AAG CAG AGA CGG GAA      1197
Ser Gly Met Gln Ile Ala Leu Asn Asp His Leu Lys Gln Arg Arg Glu
305                 310                 315                 320

GTG GCC AAA ACC GTC TTT TGC CTG GTC CTT GTC TTT GCC CTC TGC TGG      1245
Val Ala Lys Thr Val Phe Cys Leu Val Leu Val Phe Ala Leu Cys Trp
            325                 330                 335

CTT CCC CTT CAC CTC AGC AGG ATT CTG AAG CTC ACT CTT TAT AAT CAG      1293
Leu Pro Leu His Leu Ser Arg Ile Leu Lys Leu Thr Leu Tyr Asn Gln
            340                 345                 350

AAT GAT CCC AAT AGA TGT GAA CTT TTG AGC TTT CTG TTG GTA TTG GAC      1341
Asn Asp Pro Asn Arg Cys Glu Leu Leu Ser Phe Leu Leu Val Leu Asp
            355                 360                 365

TAT ATT GGT ATC AAC ATG GCT TCA CTG AAT TCC TGC ATT AAC CCA ATT      1389
Tyr Ile Gly Ile Asn Met Ala Ser Leu Asn Ser Cys Ile Asn Pro Ile
            370                 375                 380

GCT CTG TAT TTG GTG AGC AAA AGA TTC AAA AAC TGC TTT AAG TCA TGC      1437
Ala Leu Tyr Leu Val Ser Lys Arg Phe Lys Asn Cys Phe Lys Ser Cys
385                 390                 395                 400

TTA TGC TGC TGG TGC CAG TCA TTT GAA GAA AAA CAG TCC TTG GAG GAA      1485
Leu Cys Cys Trp Cys Gln Ser Phe Glu Glu Lys Gln Ser Leu Glu Glu
            405                 410                 415

AAG CAG TCG TGC TTA AAG TTC AAA GCT AAT GAT CAC GGA TAT GAC AAC      1533
Lys Gln Ser Cys Leu Lys Phe Lys Ala Asn Asp His Gly Tyr Asp Asn
            420                 425                 430

TTC CGT TCC AGT AAT AAA TAC AGC TCA TCT TGAAAGAAGA ACTATTCACT        1583
Phe Arg Ser Ser Asn Lys Tyr Ser Ser Ser
            435                 440

GTATTTCATT TTCTTTATAT TGGACCGAAG TCATTAAAAC AAAATGAAAC ATTTGCCAAA    1643

ACAAAACAAA AAACTATGTA TTTGCACAGC ACACTATTAA AATATTAAGT GTAATTATTT    1703

TAACACTCAC AGCTACATAT GACATTTTAT GAGCTGTTTA CGGCATGGAA AGAAAATCAG    1763

TGGGAATTAA GAAAGCCTCG TCGTGAAAGC ACTTAATTTT TTACAGTTAG CACTTCAACA    1823

TAGCTCTTAA CAACTTCCAG GATATTCACA CAACACTTAG GCTTAAAAAT GAGCTCACTC    1883

AGAATTTCTA TTCTTTCTAA AAAGAGATTT ATTTTTAAAT CAATGGGACT CTGATATAAA    1943

GGAAGAATAA GTCACTGTAA AACAGAACTT TTAAATGAAG CTTAAATTAC TCAATTTAAA    2003

ATTTTAAAAT CCTTTAAAAC AACTTTTCAA TTAATATTAT CACACTATTA TCAGATTGTA    2063

ATTAGATGCA AATGAGAGAG CAGTTTAGTT GTTGCATTTT TCGGACACTG GAAACATTTA    2123

AATGATCAGG AGGGAGTAAC AGAAAGAGCA AGGCTGTTTT TGAAAATCAT TACACTTTCA    2183

CTAGAAGCCC AAACCTCAGC ATTCTGCAAT ATGTAACCAA CATGTCACAA ACAAGCAGCA    2243

TGTAACAGAC TGGCACATGT GCCAGCTGAA TTTAAAATAT AATACTTTTA AAAGAAAAT    2303

TATTACATCC TTTACATTCA GTTAAGATCA AACCTCACAA AGAGAAATAG AATGTTTGAA    2363

AGGCTATCCC AAAAGACTTT TTTGAATCTG TCATTCACAT ACCCTGTGAA GACAATACTA    2423
```

```
TCTACAATTT TTTCAGGATT ATTAAAATCT TCTTTTTTCA CTATCGTAGC TTAAACTCTG    2483

TTTGGTTTTG TCATCTGTAA ATACTTACCT ACATACACTG CATGTAGATG ATTAAATGAG    2543

GGCAGGCCCT GTGCTCATAG CTTTACGATG GAGAGATGCC AGTGACCTCA TAATAAAGAC    2603

TGTGAACTGC CTGGTGCAGT GTCCACATGA CAAAGGGGCA GGTAGCACCC TCTCTCACCC    2663

ATGCTGTGGT TAAAATGGTT TCTAGCATAT GTATAATGCT ATAGTTAAAA TACTATTTTT    2723

CAAAATCATA CAGATTAGTA CATTTAACAG CTACCTGTAA AGCTTATTAC TAATTTTTGT    2783

ATTATTTTTG TAAATAGCCA ATAGAAAAGT TTGCTTGACA TGGTGCTTTT CTTTCATCTA    2843

GAGGCAAAAC TGCTTTTTGA GACCGTAAGA ACCTCTTAGC TTTGTGCGTT CCTGCCTAAT    2903

TTTTATATCT TCTAAGCAAA GTGCCTTAGG ATAGCTTGGG ATGAGATGTG TGTGAAAGTA    2963

TGTACAAGAG AAAACGGAAG AGAGAGGAAA TGAGGTGGGG TTGGAGGAAA CCCATGGGGA    3023

CAGATTCCCA TTCTTAGCCT AACGTTCGTC ATTGCCTCGT CACATCAATG CAAAAGGTCC    3083

TGATTTTGTT CCAGCAAAAC ACAGTGCAAT GTTCTCAGAG TGACTTTCGA ATAAATTGG    3143

GCCCAAGAGC TTTAACTCGG TCTTAAAATA TGCCCAAATT TTTACTTTGT TTTTCTTTTA    3203

ATAGGCTGGG CCACATGTTG GAAATAAGCT AGTAATGTTG TTTTCTGTCA ATATTGAATG    3263

TGATGGTACA GTAAACCAAA ACCCAACAAT GTGGCCAGAA AGAAAGAGCA ATAATAATTA    3323

ATTCACACAC CATATGGATT CTATTTATAA ATCACCCACA AACTTGTTCT TTAATTTCAT    3383

CCCAATCACT TTTTCAGAGG CCTGTTATCA TAGAAGTCAT TTTAGACTCT CAATTTTAAA    3443

TTAATTTTGA ATCACTAATA TTTTCACAGT TTATTAATAT ATTTAATTTC TATTTAAATT    3503

TTAGATTATT TTTATTACCA TGTACTGAAT TTTTACATCC TGATACCCTT TCCTTCTCCA    3563

TGTCAGTATC ATGTTCTCTA ATTATCTTGC CAAATTTTGA AACTACACAC AAAAAGCATA    3623

CTTGCATTAT TTATAATAAA ATTGCATTCA GTGGCTTTTT AAAAAAAATG TTTGATTCAA    3683

AACTTTAACA TACTGATAAG TAAGAAACAA TTATAATTTC TTTACATACT CAAAACCAAG    3743

ATAGAAAAAG GTGCTATCGT TCAACTTCAA AACATGTTTC CTAGTATTAA GGACTTTAAT    3803

ATAGCAACAG ACAAAATTAT TGTTAACATG GATGTTACAG CTCAAAAGAT TTATAAAGA    3863

TTTTAACCTA TTTTCTCCCT TATTATCCAC TGCTAATGTG GATGTATGTT CAAACACCTT    3923

TTAGTATTGA TAGCTTACAT ATGGCCAAAG GAATACAGTT TATAGCAAAA CATGGGTATG    3983

CTGTAGCTAA CTTTATAAAA GTGTAATATA ACAATGTAAA AAATTATATA TCTGGGAGGA    4043

TTTTTTGGTT GCCTAAAGTG GCTATAGTTA CTGATTTTTT ATTATGTAAG CAAAACCAAT    4103

AAAAATTTAA GTTTTTTTAA CAACTACCTT ATTTTTCACT GTACAGACAC TAATTCATTA    4163

AATACTAATT GATTGTTTAA AAGAAATATA AATGTGACAA GTGGACATTA TTTATGTTAA    4223

ATATACAATT ATCAAGCAAG TATGAAGTTA TTCAATTAAA ATGCCACATT TCTGGTCTCT    4283

GGGAAAAAAA AAAAAAAA                                                  4301
```

(2) INFORMATION FOR SEQ ID NO:4:

(i) SEQUENCE CHARACTERISTICS:
        (A) LENGTH: 442 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gln Pro Pro Ser Leu Cys Gly Arg Ala Leu Val Ala Leu Val
 1               5                  10                  15
```

```
Leu Ala Cys Gly Leu Ser Arg Ile Trp Gly Glu Arg Gly Phe Pro
            20                  25                  30

Pro Asp Arg Ala Thr Pro Leu Leu Gln Thr Ala Glu Ile Met Thr Pro
            35                  40                  45

Pro Thr Lys Thr Leu Trp Pro Lys Gly Ser Asn Ala Ser Leu Ala Arg
        50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
            100                 105                 110

Val Leu Gly Ile Ile Gly Asn Ser Thr Leu Leu Arg Ile Ile Tyr Lys
            115                 120                 125

Asn Lys Cys Met Arg Asn Gly Pro Asn Ile Leu Ile Ala Ser Leu Ala
130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
            165                 170                 175

Val Pro Phe Ile Gln Lys Ala Ser Val Gly Ile Thr Val Leu Ser Leu
            180                 185                 190

Cys Ala Leu Ser Ile Asp Arg Tyr Arg Ala Val Ala Ser Trp Ser Arg
            195                 200                 205

Ile Lys Gly Ile Gly Val Pro Lys Trp Thr Ala Val Glu Ile Val Leu
            210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
            245                 250                 255

Leu His Pro Val Gln Lys Thr Ala Phe Met Gln Phe Tyr Lys Thr Ala
            260                 265                 270

Lys Asp Trp Trp Leu Phe Ser Phe Tyr Phe Cys Leu Pro Leu Ala Ile
            275                 280                 285

Thr Ala Phe Phe Tyr Thr Leu Met Thr Cys Glu Met Leu Arg Lys Lys
            290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
            325                 330                 335

Leu Pro Leu His Leu Ser Arg Ile Leu Lys Leu Thr Leu Tyr Asn Gln
            340                 345                 350

Asn Asp Pro Asn Arg Cys Glu Leu Leu Ser Phe Leu Leu Val Leu Asp
            355                 360                 365

Tyr Ile Gly Ile Asn Met Ala Ser Leu Asn Ser Cys Ile Asn Pro Ile
            370                 375                 380

Ala Leu Tyr Leu Val Ser Lys Arg Phe Lys Asn Cys Phe Lys Ser Cys
385                 390                 395                 400

Leu Cys Cys Trp Cys Gln Ser Phe Glu Glu Lys Gln Ser Leu Glu Glu
            405                 410                 415
```

```
Lys Gln Ser Cys Leu Lys Phe Lys Ala Asn Asp His Gly Tyr Asp Asn
            420                 425                 430

Phe Arg Ser Ser Asn Lys Tyr Ser Ser Ser
            435             440
```